US009994617B2

(12) United States Patent
Tite et al.

(10) Patent No.: US 9,994,617 B2
(45) Date of Patent: Jun. 12, 2018

(54) MODULATION OF STRUCTURED POLYPEPTIDE SPECIFICITY

(71) Applicant: BICYCLE THERAPEUTICS LIMITED, Cambridge (GB)

(72) Inventors: John Tite, Cambridge (GB); Edward Walker, Cambridge (GB); Catherine Stace, Cambridge (GB); Christian Heinis, Bern (CH)

(73) Assignee: BicycleRD Limited, Cambridge (GB)

( * ) Notice: Subject to any disclaimer, the term of this patent is extended or adjusted under 35 U.S.C. 154(b) by 0 days. days.

(21) Appl. No.: 14/350,263

(22) PCT Filed: Oct. 8, 2012

(86) PCT No.: PCT/EP2012/069897
§ 371 (c)(1),
(2) Date: Apr. 7, 2014

(87) PCT Pub. No.: WO2013/050615
PCT Pub. Date: Apr. 11, 2013

(65) Prior Publication Data
US 2014/0249292 A1 Sep. 4, 2014

(30) Foreign Application Priority Data

Oct. 7, 2011 (GB) .................................. 1117408.3
Mar. 29, 2012 (GB) .................................. 1205612.3

(51) Int. Cl.
| | |
|---|---|
| *A61K 38/10* | (2006.01) |
| *A61K 38/12* | (2006.01) |
| *A61K 38/04* | (2006.01) |
| *C07K 5/00* | (2006.01) |
| *C07K 7/00* | (2006.01) |
| *C07K 16/00* | (2006.01) |
| *C07K 17/00* | (2006.01) |
| *C07K 7/56* | (2006.01) |
| *C07K 7/08* | (2006.01) |
| *C07K 1/00* | (2006.01) |
| *C07K 2/00* | (2006.01) |
| *C07K 1/107* | (2006.01) |

(52) U.S. Cl.
CPC ............... *C07K 7/56* (2013.01); *A61K 38/10* (2013.01); *A61K 38/12* (2013.01); *C07K 1/00* (2013.01); *C07K 1/1075* (2013.01); *C07K 2/00* (2013.01); *C07K 7/08* (2013.01)

(58) Field of Classification Search
None
See application file for complete search history.

(56) References Cited

U.S. PATENT DOCUMENTS

| | | | | |
|---|---|---|---|---|
| 8,685,890 | B2 * | 4/2014 | Winter et al. | 506/9 |
| 8,778,844 | B2 * | 7/2014 | Winter et al. | 506/9 |
| 2006/0019900 | A1 | 1/2006 | Lam et al. | |
| 2008/0313749 | A1 | 12/2008 | Timmerman et al. | |
| 2010/0317547 | A1 * | 12/2010 | Gregory et al. | 506/17 |
| 2014/0163201 | A1 * | 6/2014 | Winter et al. | 530/324 |
| 2014/0187757 | A1 * | 7/2014 | Winter et al. | 530/402 |
| 2014/0256596 | A1 * | 9/2014 | Tite et al. | 506/18 |

OTHER PUBLICATIONS

U.S. Appl. No. 14/242,544, filed Apr. 2014, Winter et al.*
Gentilucci et al., Curr. Pharma. Design 16:3185-3203 (2010).*
Baeriswyl, et al., "Bicyclic Peptides with Optimized Ring Size Inhibit Human Plasma Kallikrein and its Orthologues While Sparing Paralogous Proteases", ChemMedChem Communications, 7:1173-76 (2012).
Man, et al., "Prediction of the odorant binding site of olfactory receptor proteins by human-mouse comparisons", Protein Science, 13:240-54 (2004).
Peterson, et al., "Evolutionary constraints on structural similarity in orthologs and paralogs", Protein Science, 18:1306-15 (2009).
PCT International Preliminary Search Report for PCT/EP2012/069897 dated Apr. 17, 2014.
PCT International Search Report and Written Opinion for PCT/EP2012/069897 dated Jan. 24, 2013.

* cited by examiner

*Primary Examiner* — Hasan Ahmed
*Assistant Examiner* — Thea D'Ambrosio
(74) *Attorney, Agent, or Firm* — Convergent Law Group LLP

(57) ABSTRACT

The invention describes a method for selecting a polypeptide ligand having a desired level of specificity for a target, wherein the polypeptide ligand comprises a polypeptide comprising at least three reactive groups, separated by at least two loop sequences, and a molecular scaffold which forms covalent bonds with the reactive groups of the polypeptide such that at least two polypeptide loops are formed on the molecular scaffold, comprising (i) screening at least two different sets of polypeptide ligands against the target, and selecting one or more ligands from each library which interact with the target; (ii) comparing the activity of the selected ligands with one or more paralogues or orthologues of the target; and (iii) further selecting one or more ligands according to their activity towards said one or more paralogues or orthologues; wherein said two or more different sets of ligands differ in the length of the polypeptide loops formed on the molecular scaffold.

5 Claims, 14 Drawing Sheets

|              | LOOP 1            | LOOP 2            |                          |
|--------------|-------------------|-------------------|--------------------------|
| LIBRARY 5x5  | A [C] X X X X X   | [C] X X X X X [C] A | [SEQ ID NO. 45] – PHAGE PIII |
| LIBRARY 3x3 A | A [C] X X X [C] X X X [C] A | | [SEQ ID NO. 46] – PHAGE PIII |
| LIBRARY 3x3 B | X [C] X X X [C] X X X [C] X | | [SEQ ID NO. 47] – PHAGE PIII |

| CLONE: | AMINO ACID SEQUENCE: | | | | | | | | | | | | | | | |
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | |
| PK100 | A | C | A | W | P | A | R | C | L | T | V | B | L | C | A | SEQ ID NO. 22 |
| PK101 | A | C | R | W | P | A | R | C | V | H | Q | D | L | C | A | SEQ ID NO. 23 |
| PK102 | A | C | R | W | P | A | R | C | L | T | T | S | L | C | A | SEQ ID NO. 25 |
| PK103 | A | C | A | W | P | A | K | C | L | T | R | E | L | C | A | SEQ ID NO. 37 |
| PK104 | A | C | A | W | P | A | R | C | L | T | T | S | L | C | G | SEQ ID NO. 35 |
| PK105 | A | C | S | W | P | A | R | C | N | H | Q | B | L | C | A | SEQ ID NO. 24 |
| PK106 | A | C | R | W | P | A | R | C | T | H | Q | N | Y | C | A | SEQ ID NO. 26 |
| PK107 | A | C | T | W | P | A | R | C | T | H | Q | N | W | C | A | SEQ ID NO. 27 |
| PK108 | A | C | T | W | P | A | R | C | T | M | Q | N | W | C | A | SEQ ID NO. 33 |
| PK109 | A | C | S | W | P | Y | R | C | L | H | Q | R | Y | C | A | SEQ ID NO. 31 |
| PK110 | A | C | N | W | P | Y | R | C | L | H | T | R | L | C | A | SEQ ID NO. 30 |
| PK111 | A | C | G | V | P | Y | R | C | T | H | Q | E | M | C | A | SEQ ID NO. 32 |
| PK112 | A | C | T | Y | P | Y | K | C | L | H | Q | N | L | C | A | SEQ ID NO. 36 |
| PK113 | A | C | A | D | P | W | A | C | L | F | R | R | P | C | A | SEQ ID NO. 34 |
| PK114 | A | C | G | G | P | Q | N | C | R | T | W | T | T | C | A | SEQ ID NO. 29 |
| PK115 | A | C | G | G | Y | N | N | C | R | A | F | S | Y | C | A | SEQ ID NO. 38 |
| PK116 | A | C | F | P | S | H | D | C | D | G | R | R | M | C | A | SEQ ID NO. 28 |

FIG. 1C

| CLONE: | AMINO ACID SEQUENCE: | | | | | | | | | | |
|---|---|---|---|---|---|---|---|---|---|---|---|
| | 1 | 2 | 3 | 4 | 5 | 6 | 7 | 8 | 9 | 10 | 11 |
| PK117 | A | C | F | K | A | C | R | V | N | C | A | SEQ ID NO. 21 |
| PK118 | A | C | F | K | Q | C | R | V | N | C | A | SEQ ID NO. 19 |
| PK119 | A | C | F | K | N | C | R | V | N | C | A | SEQ ID NO. 17 |
| PK120 | A | C | F | Y | K | C | R | V | N | C | A | SEQ ID NO. 20 |
| PK121 | A | C | F | N | K | C | R | V | N | C | A | SEQ ID NO. 18 |
| PK122 | A | C | F | P | K | C | R | V | A | C | A | SEQ ID NO. 15 |
| PK123 | A | C | F | K | H | C | R | V | A | C | A | SEQ ID NO. 14 |
| PK124 | A | C | F | D | P | C | R | V | I | C | A | SEQ ID NO. 16 |

FIG. 1D

| CLONE: | AMINO ACID SEQUENCE: | | | | | | | | | | |
|---|---|---|---|---|---|---|---|---|---|---|---|
| | 1 | 2 | 3 | 4 | 5 | 6 | 7 | 8 | 9 | 10 | 11 |
| PK125 | S | C | F | N | R | C | R | V | P | C | F | SEQ ID NO. 47 |
| PK126 | K | C | F | T | A | C | R | V | D | C | F | SEQ ID NO. 48 |
| PK127 | R | C | F | N | L | C | R | V | G | C | L | SEQ ID NO. 49 |
| PK128 | D | C | F | Q | G | C | R | V | F | C | S | SEQ ID NO. 50 |
| PK129 | Q | C | F | E | L | C | R | V | V | C | L | SEQ ID NO. 51 |
| PK130 | M | C | F | D | S | C | R | V | N | C | T | SEQ ID NO. 52 |
| PK131 | S | C | F | A | L | C | R | V | P | C | Q | SEQ ID NO. 53 |
| PK132 | V | C | F | P | L | C | R | V | P | C | I | SEQ ID NO. 54 |
| PK133 | V | C | F | G | V | C | R | V | L | C | A | SEQ ID NO. 55 |
| PK134 | K | C | F | Q | A | C | R | V | S | C | Y | SEQ ID NO. 56 |
| PK135 | V | C | F | S | L | C | R | A | G | C | L | SEQ ID NO. 57 |
| PK136 | R | C | F | E | K | C | R | A | F | C | Y | SEQ ID NO. 58 |
| PK137 | R | C | W | Q | T | C | R | V | S | C | V | SEQ ID NO. 59 |
| PK138 | L | C | W | T | G | C | R | V | S | C | F | SEQ ID NO. 60 |
| PK139 | G | C | W | A | P | C | R | V | G | C | Y | SEQ ID NO. 61 |
| PK140 | R | C | W | T | A | C | R | G | L | C | F | SEQ ID NO. 62 |
| PK141 | D | C | Y | Q | L | C | R | V | S | C | E | SEQ ID NO. 63 |
| PK142 | T | C | F | R | S | C | K | V | A | C | Y | SEQ ID NO. 64 |
| PK143 | Q | C | F | Q | A | C | K | T | L | C | W | SEQ ID NO. 65 |

FIG. 1E

MODULATION OF STRUCTURED POLYPEPTIDE SPECIFICITY

CROSS REFERENCE TO RELATED APPLICATIONS

This application is a national phase filing under 35 U.S.C. 371 of International Patent Application No. PCT/EP2012/069897, filed Oct. 8, 2012, which claims the benefit of GB Application No. 1205612.3, filed Mar. 29, 2012, and GB Application No. 1117408.3, filed Oct. 7, 2011, and is incorporated herein by reference.

The present invention relates to polypeptides which are complexed to molecular scaffolds such that two or more peptide loops are subtended between attachment points to the scaffold. In particular, the invention describes methods for modulating the specificity of the polypeptide complexes for their cognate targets by varying the length of the loops subtended on the scaffold.

Cyclic peptides are able to bind with high affinity and target specificity to protein targets and hence are an attractive molecule class for the development of therapeutics. In fact, several cyclic peptides are already successfully used in the clinic, such as for example the antibacterial peptide vancomycin, the immunosuppressant drug cyclosporine or the anti-cancer drug ocreotide (Driggers, et al., *Nat Rev Drug Discov* 2008, 7 (7), 608-24). The good binding properties of cyclic peptides result from a relatively large interaction surface formed between the peptide and the target as well as the reduced conformational flexibility of the cyclic structures. Typically, macrocycles bind to surfaces of several hundred square angstrom, such as for example the cyclic peptide CXCR4 antagonist CVX15 (400 Å$^2$; Wu, B., et al., *Science* 330 (6007), 1066-71), a cyclic peptide with the Arg-Gly-Asp motif binding to integrin αVb3 (355 Å$^2$; Xiong, J. P., et al., *Science* 2002, 296 (5565), 151-5) or the cyclic peptide inhibitor upain-1 binding to urokinase-type plasminogen activator (603 Å$^2$; Zhao, G., et al., *J Struct Biol* 2007, 160 (1), 1-10).

Due to their cyclic configuration, peptide macrocycles are less flexible than linear peptides, leading to a smaller loss of entropy upon binding to targets and resulting in a higher binding affinity. The reduced flexibility is also responsible for locking target-specific conformations, which increases the binding specificity compared to linear peptides. This effect is exemplified by a potent and selective inhibitor of matrix metalloproteinase 8 (MMP-8) which loses its selectivity over other MMPs when its ring is opened (Cherney, R. J., et al., *J Med Chem* 1998, 41 (11), 1749-51). The favorable binding properties achieved through macrocyclization are even more pronounced in multicyclic peptides having more than one peptide ring as for example in vancomycin, nisin or actinomycin.

Different research teams have previously tethered polypeptides with cysteine residues to a synthetic molecular structure (Kemp, D. S. and McNamara, P. E., J. Org. Chem, 1985; Timmerman, P. et al., ChemBioChem, 2005). Meloen and co-workers had used tris(bromomethyl)benzene and related molecules for rapid and quantitative cyclisation of multiple peptide loops onto synthetic scaffolds for structural mimicry of protein surfaces (Timmerman, P. et al., ChemBioChem, 2005). Methods for the generation of candidate drug compounds wherein said compounds are generated by linking cysteine containing polypeptides to a molecular scaffold as for example tris(bromomethyl)benzene are disclosed in WO 2004/077062 and WO 2006/078161.

WO2004/077062 discloses a method of selecting a candidate drug compound. In particular, this document discloses various scaffold molecules comprising first and second reactive groups, and contacting said scaffold with a further molecule to form at least two linkages between the scaffold and the further molecule in a coupling reaction.

WO2006/078161 discloses binding compounds, immunogenic compounds and peptidomimetics. This document discloses the artificial synthesis of various collections of peptides taken from existing proteins. These peptides are then combined with a constant synthetic peptide having some amino acid changes introduced in order to produce combinatorial libraries. By introducing this diversity via the chemical linkage to separate peptides featuring various amino acid changes, an increased opportunity to find the desired binding activity is provided. FIG. 1 of this document shows a schematic representation of the synthesis of various loop peptide constructs. The constructs disclosed in this document rely on —SH functionalised peptides, typically comprising cysteine residues, and heteroaromatic groups on the scaffold, typically comprising benzylic halogen substituents such as bis- or tris-bromophenylbenzene. Such groups react to form a thioether linkage between the peptide and the scaffold.

We recently developed a phage display-based combinatorial approach to generate and screen large libraries of bicyclic peptides to targets of interest (Heinis, et al., *Nat Chem Biol* 2009, 5 (7), 502-7; see also international patent application WO2009/098450). Briefly, combinatorial libraries of linear peptides containing three cysteine residues and two regions of six random amino acids (Cys-(Xaa)$_6$-Cys-(Xaa)$_6$-Cys) were displayed on phage and cyclised by covalently linking the cysteine side chains to a small molecule (tris-(bromomethyl)benzene). Bicyclic peptides isolated in affinity selections to the human proteases cathepsin G and plasma kallikrein (PK) had nanomolar inhibitory constants. The best inhibitor, PK15, inhibits human PK (hPK) with a $K_i$ of 3 nM. Similarities in the amino acid sequences of several isolated bicyclic peptides suggested that both peptide loops contribute to the binding. PK15 did not inhibit rat PK (81% sequence identity) nor the homologous human serine proteases factor XIa (hfXIa; 69% sequence identity) or thrombin (36% sequence identity) at the highest concentration tested (10 µM) (Heinis, et al., *Nat Chem Biol* 2009, 5 (7), 502-7). This finding suggested that the bicyclic inhibitor is highly specific and that other human trypsin-like serine proteases will not be inhibited. A synthetic, small peptidic inhibitor such as PK15 having the above described potency and target selectivity has potential application as a therapeutic to control PK activity in hereditary angioedema, a life-threatening disease which is characterized by recurrent episodes of edema or to prevent contact activation in cardiopulmonary bypass surgery. However, the absence of inhibitory activity towards murine PK prevents the preclinical testing of PK15 in small laboratory animals.

High specificity may be a desirable characteristic in a reagent or a therapeutic agent, but specificity which excludes activity against nearest homologues from other species impedes experiments and tests which are normally conducted on laboratory animals, in preparation for human trials. In some fields, such as antibody therapy, similar problems are often addressed by generating surrogate antibodies which are designed to have similar binding properties to the therapeutic candidate, but an immunogenic profile relevant to a laboratory animal. No such approach, however, exists in the field of structured polypeptides.

SUMMARY OF THE INVENTION

We have analysed the specificity of structured polypeptides selected against the same target from libraries of varying loop length. We have found that longer loops, in other words polypeptides wherein more amino acids are present between scaffold attachment points, result in a higher level of specificity. Conversely, polypeptides with shorter loops are less specific. Selection of the appropriate loop length can therefore lead to polypeptides having the desired level of specificity.

In accordance with a first aspect, there is provided a method for selecting a polypeptide ligand having a desired level of specificity for a target, wherein the polypeptide ligand comprises a polypeptide comprising at least three reactive groups, separated by at least two loop sequences, and a molecular scaffold which forms covalent bonds with the reactive groups of the polypeptide such that at least two polypeptide loops are formed on the molecular scaffold, comprising
(i) screening at least two different sets of polypeptide ligands against the target, and selecting one or more ligands from each set which interact with the target;
(ii) comparing the activity of the selected ligands with one or more paralogues or orthologues of the target; and
(iii) further selecting one or more ligands according to their activity towards said one or more paralogues or orthologues; wherein said two or more different sets of ligands differ in the length of the polypeptide loops formed on the molecular scaffold.

We have found that, by tuning the loop length of the polypeptide ligands, we can select polypeptide ligands which can differentiate between a paralogue and an orthologue of a given target. This means that ligands can be isolated which are active against orthologous targets, that is equivalents of the target from other species, but not paralogues, which are entities closely related to the target, potentially in the same species, which have a different function. For example, ligands can be isolated which inhibit human and rat plasma kallikrein, but not the structurally similar human factor XIa.

The ligands may be monospecific, bispecific or multispecific. Thus, the ligands may bind a single target, or two or more targets. Where two or more targets are bound, it is only necessary for one of said targets to be shared, for the specificity of the ligands for that target to be selected for by the methods described herein.

The sets of ligands can be arranged in separate libraries, for example a library of ligands having loops three amino acids long and a library of ligands having loops four amino acids long. Alternatively, the sets can be present in a single library.

In one embodiment, the sets comprise polypeptide ligands in which the loop lengths are equal, that is to say each ligand has loops of equal length. However, ligands within the different sets have loops of differing length. Thus, one set may contain ligands having loops three amino acids long and another set may contain ligands having loops four amino acids long. The sets may screened separately, or combined into a single library.

In one embodiment, the first and second libraries comprise polypeptide ligands having a loop length of between three and six amino acids, provided that the loop length in the second library is not equal to that in the first.

In one embodiment, the polypeptide ligands in each or one set comprise two loops. Alternatively, or in addition, the polypeptide ligands in each or one set comprise three loops. Four, five or more loops are also possible.

In one embodiment, the selected ligands are active towards orthologues of the target, but inactive or less active towards paralogues.

In order to increase the selectivity for cross-reaction with orthologues but not paralogues, the sets of ligands can be further screened against one or more paralogues of the target, and ligands showing activity towards the one or more paralogues can be discarded.

In one embodiment, the screening against the paralogues is performed before the screen against the target.

To the same end, sets of ligands can be further screened against one or more orthologues of the target, and ligands showing activity towards one or more orthologues can be retained.

The activity which is screened for can be any activity, including a binding activity, an enzymatic activity, an inhibitory activity, a catalytic activity or any other measurable chemical or biological activity.

In a further embodiment, there is provided a group of polypeptide ligands each of which comprises at least three reactive groups, separated by at least two loop sequences, which are attached to a molecular scaffold which forms covalent bonds with the reactive groups of the polypeptide such that at least two polypeptide loops are formed on the molecular scaffold, wherein:
(i) at least two of the ligands are specific for the same target; and
(ii) at least two ligands specific for the same target comprise loops of different lengths and differ in their specificity for the target.

A group of polypeptide ligands comprises at least two ligands. It may comprise a large number of ligands, and be synonymous with a library; however, in most embodiments it is envisaged that the group will consist of a few ligands, that is two, three, four or five ligands.

In one embodiment, all of the ligands in the group are specific for the same target. This can occur, for example, as a result of pre-screening of the group against the target. In one embodiment, the group may consist of few ligands, for example only two, three or four ligands, which have been selected by screening against the target.

In one embodiment, the ligands each possess two or three polypeptide loops.

The loops of the polypeptide ligands can be substantially any length. In one embodiment, the polypeptide loops are three, four, five or six amino acids in length.

It is possible for loop length to be mixed in a single polypeptide ligand. Thus, a ligand could have one loop of three amino acids and another of four. However, in one embodiment at least two loops in each individual polypeptide, or at least three, at least four or all loops in each individual polypeptide, are the same length.

In accordance with a second aspect, there is provided a method for producing a mutant polypeptide ligand to produce an improved level of binding activity for a target over that of a parent polypeptide ligand, wherein the parent polypeptide ligand comprises a polypeptide comprising at least three reactive groups, separated by at least two loop sequences, and a molecular scaffold which forms covalent bonds with the reactive groups of the polypeptide such that at least two polypeptide loops are formed on the molecular scaffold, comprising the steps of: (a) for each of two or more amino acid positions in each of the loop sequences, producing n different libraries of mutants, each library consisting of parent polypeptides in which one of said amino acid positions in the loop sequence has been mutated by replacement with one of n different non-parental amino acids; (b) screening each library for binding to the parental target, and scoring each mutation; (c) identifying the amino acid positions at which mutations are tolerated; (d) producing one or more mutant polypeptides comprising one or more mutations located at the amino acid positions identified in step (c).

In one embodiment, step (d) comprises preparing a library comprising polypeptides which incorporate mutations at two or more of the amino acid positions identified in step (c), and screening the library for polypeptides with an improved level of binding activity for the target.

The value of n can be selected according to the number of different mutants it is intended to create in each library. For example, if mutants comprising all possible natural amino acids are desired, n can be 20. If non-natural amino acids are included, such as N-methylated amino acids, n can be greater than 20, such as 22 or 23. For example, n can be 2 or more; 3, 4, 5, 6, 7, 8, 9, 10, 11, 12, 13, 14, 15, 16, 17, 18, 19 or 20.

In a third aspect, there is provided a library of polypeptide ligands, wherein the polypeptide ligands comprise a polypeptide comprising at least three reactive groups, separated by at least two loop sequences, and a molecular scaffold which forms covalent bonds with the reactive groups of the polypeptide such that at least two polypeptide loops are formed on the molecular scaffold, said library consisting of m different mutants of a polypeptide ligand in which a defined amino acid position in the loop sequences has been mutated by replacement with one of m different amino acids, wherein m is at least 2.

In a fourth aspect, there is provided a set of libraries of polypeptide ligands, wherein the polypeptide ligands comprise a polypeptide comprising at least three reactive groups, separated by at least two loop sequences, and a molecular scaffold which forms covalent bonds with the reactive groups of the polypeptide such that at least two polypeptide loops are formed on the molecular scaffold, which set comprises two or more libraries of polypeptide ligands, each of said libraries of polypeptide ligands consisting of m different mutants of a polypeptide ligand in which a defined amino acid position in the loop sequences has been mutated by replacement with one of m different amino acids.

Preferably, m is between 2 and 20; in embodiments, m is at least 3, 4, 5, 6, 7, 8, 9, 10, 11, 12, 13, 14, 15, 16, 17, 18, 19 or 20, or more, as set out in respect of n above.

In a further aspect, there is provided a polypeptide ligand, a group of polypeptide ligands or a library of polypeptide ligands according to the preceding aspect of the invention, which comprises one or more non-natural amino acid substituents and is resistant to protease degradation.

We have found that certain modified amino acids permit highly specific binding to the designated target with nM Ki, whilst increasing residence time in plasma significantly.

In one embodiment, the modified amino acid is selected from N-methyl Arginine, homoarginine and hydroxyproline. Preferably, N-methyl and homo-derivatives of Arginine are used to replace Arginine, and hydroxyproline replaces tryptophan. In another embodiment, R may be replaced with guanidyl-phenylalanine.

DETAILED DESCRIPTION OF THE INVENTION

Figures 1A, 1B:
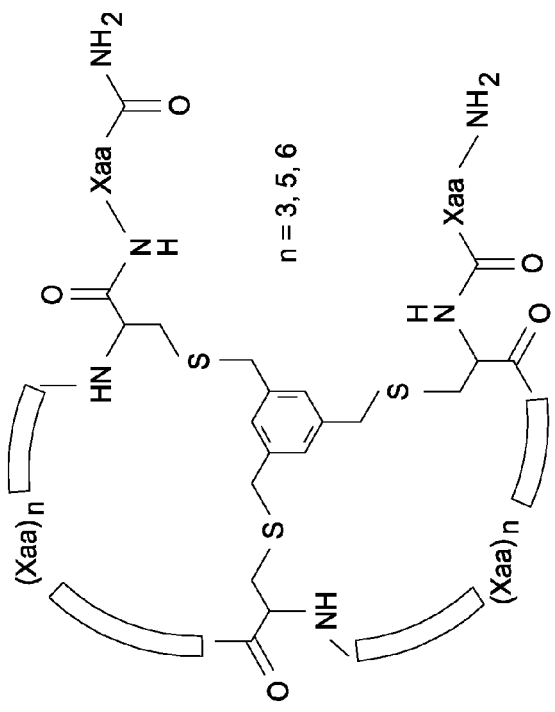
FIG. 1 Phage selection of bicyclic peptides. (a) Bicyclic peptide phage libraries. Random amino acids are indicated as 'X', alanine as 'A' and the constant three cysteine residues as 'C'. (b) Format of chemically synthesized bicyclic peptide structures having loops of 3, 5 or 6 amino acids. The structures are generated by linking linear peptides via three cysteine side chains to tris-(bromomethly)benzene (TBMB). Amino acids that vary in the bicyclic peptides are indicated with 'Xaa'. (c-e) Sequences of bicyclic peptides isolated from library 5×5 (c), library 3×3 A (d) and library 3×3 B (e). Similarities in amino acids are highlighted by shading.

Unless defined otherwise, all technical and scientific terms used herein have the same meaning as commonly understood by those of ordinary skill in the art, such as in the arts of peptide chemistry, cell culture and phage display, nucleic acid chemistry and biochemistry. Standard techniques are used for molecular biology, genetic and biochemical methods (see Sambrook et al., Molecular Cloning: A Laboratory Manual, 3rd ed., 2001, Cold Spring Harbor Laboratory Press, Cold Spring Harbor, N.Y.; Ausubel et al., Short Protocols in Molecular Biology (1999) $4^{th}$ ed., John Wiley & Sons, Inc.), which are incorporated herein by reference.

A peptide ligand, as referred to herein, refers to a peptide covalently bound to a molecular scaffold. Typically, such peptides comprise two or more reactive groups which are capable of forming covalent bonds to the scaffold, and a sequence subtended between said reactive groups which is referred to as the loop sequence, since it forms a loop when the peptide is bound to the scaffold. In the present case, the peptides comprise at least three reactive groups, and form at least two loops on the scaffold.

The reactive groups are groups capable of forming a covalent bond with the molecular scaffold. Typically, the reactive groups are present on amino acid side chains on the peptide. Examples are amino-containing groups such as cysteine, lysine and selenocysteine.

Specificity, in the context herein, refers to the ability of a ligand to bind or otherwise interact with its cognate target to the exclusion of entities which are similar to the target. For example, specificity can refer to the ability of a ligand to inhibit the interaction of a human enzyme, but not a homologous enzyme from a different species. Using the approach described herein, specificity can be modulated, that is increased or decreased, so as to make the ligands more or less able to interact with homologues or paralogues of the intended target. Specificity is not intended to be synonymous with activity, affinity or avidity, and the potency of the action of a ligand on its target (such as, for example, binding affinity or level of inhibition) are not necessarily related to its specificity.

Binding activity, as used herein, refers to quantitative binding measurements taken from binding assays, for example as described herein. Therefore, binding activity refers to the amount of peptide ligand which is bound at a given target concentration.

Multispecificity is the ability to bind to two or more targets. Typically, binding peptides are capable of binding to a single target, such as an epitope in the case of an antibody, due to their conformational properties. However, peptides can be developed which can bind to two or more targets; dual specific antibodies, for example, as known in the art as referred to above. In the present invention, the peptide ligands can be capable of binding to two or more targets and are therefore be multispecific. Preferably, they bind to two targets, and are dual specific. The binding may be independent, which would mean that the binding sites for the targets on the peptide are not structurally hindered by the binding of one or other of the targets. In this case both targets can be bound independently. More generally it is expected that the binding of one target will at least partially impede the binding of the other.

There is a fundamental difference between a dual specific ligand and a ligand with specificity which encompasses two related targets. In the first case, the ligand is specific for both targets individually, and interacts with each in a specific manner. For example, a first loop in the ligand may bind to a first target, and a second loop to a second target. In the second case, the ligand is non-specific because it does not differentiate between the two targets, for example by interacting with an epitope of the targets which is common to both.

In the context of the present invention, it is possible that a ligand which has activity in respect of, for example, a target and an orthologue, could be a bispecific ligand. However, in one embodiment the ligand is not bispecific, but has a less precise specificity such that it binds both the target and one or more orthologues. In general, a ligand which has not been selected against both a target and its orthologue is less likely to be bispecific as a result of modulation of loop length.

If the ligands are truly bispecific, in one embodiment at least one of the target specificities of the ligands will be common amongst the ligands selected, and the level of that specificity can be modulated by the methods disclosed herein. Second or further specificities need not be shared, and need not be the subject of the procedures set forth herein.

A target is a molecule or part thereof to which the peptide ligands bind or otherwise interact with. Although binding is seen as a prerequisite to activity of most kinds, and may be an activity in itself, other activities are envisaged. Thus, the present invention does not require the measurement of binding directly or indirectly.

The molecular scaffold is any molecule which is able to connect the peptide at multiple points to impart one or more structural features to the peptide. It is not a cross-linker, in that it does not merely replace a disulphide bond; instead, it provides two or more attachment points for the peptide. Preferably, the molecular scaffold comprises at least three attachment points for the peptide, referred to as scaffold reactive groups. These groups are capable of reacting to the reactive groups on the peptide to form a covalent bond. Preferred structures for molecular scaffolds are described below.

Screening for binding activity (or any other desired activity) is conducted according to methods well known in the art, for instance from phage display technology. For example, targets immobilised to a solid phase can be used to identify and isolate binding members of a repertoire. Screening allows selection of members of a repertoire according to desired characteristics.

The term library refers to a mixture of heterogeneous polypeptides or nucleic acids. The library is composed of members, which are not identical. To this extent, library is synonymous with repertoire. Sequence differences between library members are responsible for the diversity present in the library. The library may take the form of a simple mixture of polypeptides or nucleic acids, or may be in the form of organisms or cells, for example bacteria, viruses, animal or plant cells and the like, transformed with a library of nucleic acids. Preferably, each individual organism or cell contains only one or a limited number of library members.

In one embodiment, the nucleic acids are incorporated into expression vectors, in order to allow expression of the polypeptides encoded by the nucleic acids. In a preferred aspect, therefore, a library may take the form of a population of host organisms, each organism containing one or more copies of an expression vector containing a single member of the library in nucleic acid form which can be expressed to produce its corresponding polypeptide member. Thus, the population of host organisms has the potential to encode a large repertoire of genetically diverse polypeptide variants.

In one embodiment, a library of nucleic acids encodes a repertoire of polypeptides. Each nucleic acid member of the library preferably has a sequence related to one or more other members of the library. By related sequence is meant an amino acid sequence having at least 50% identity, for example at least 60% identity, for example at least 70% identity, for example at least 80% identity, for example at least 90% identity, for example at least 95% identity, for example at least 98% identity, for example at least 99% identity to at least one other member of the library. Identity can be judged across a contiguous segment of at least 3 amino acids, for example at least 4, 5, 6, 7, 8, 9 or 10 amino acids, for example least 12 amino acids, for example least 14 amino acids, for example least 16 amino acids, for example least 17 amino acids or the full length of the reference sequence.

A repertoire is a collection of variants, in this case polypeptide variants, which differ in their sequence. Typically, the location and nature of the reactive groups will not vary, but the sequences forming the loops between them can be randomised. Repertoires differ in size, but should be considered to comprise at least $10^2$ members. Repertoires of $10^{11}$ or more members can be constructed.

A set of polypeptide ligands, as used herein, refers to a plurality of polypeptide ligands which can be subjected to selection in the methods described. Potentially, a set can be a repertoire, but it may also be a small collection of polypeptides, from at least 2 up to 10, 20, 50, 100 or more.

A group of polypeptide ligands, as used herein, refers to two or more ligands. In one embodiment, a group of ligands comprises only ligands which share at least one target specificity. Typically, a group will consist of from at least 2, 3, 4, 5, 6, 7, 8, 9 or 10, 20, 50, 100 or more ligands. In one embodiment, a group consists of 2 ligands.

(A) Construction of Peptide Ligands (i) Molecular Scaffold

Molecular scaffolds are described in, for example, WO2009098450 and references cited therein, particularly WO2004077062 and WO2006078161.

As noted in the foregoing documents, the molecular scaffold may be a small molecule, such as a small organic molecule.

In one embodiment the molecular scaffold may be, or may be based on, natural monomers such as nucleosides, sugars, or steroids. For example the molecular scaffold may comprise a short polymer of such entities, such as a dimer or a trimer.

In one embodiment the molecular scaffold is a compound of known toxicity, for example of low toxicity. Examples of suitable compounds include cholesterols, nucleotides, steroids, or existing drugs such as tamazepam.

In one embodiment the molecular scaffold may be a macromolecule. In one embodiment the molecular scaffold is a macromolecule composed of amino acids, nucleotides or carbohydrates.

In one embodiment the molecular scaffold comprises reactive groups that are capable of reacting with functional group(s) of the polypeptide to form covalent bonds.

The molecular scaffold may comprise chemical groups as amines, thiols, alcohols, ketones, aldehydes, nitriles, carboxylic acids, esters, alkenes, alkynes, azides, anhydrides, succinimides, maleimides, alkyl halides and acyl halides.

In one embodiment, the molecular scaffold may comprise or may consist of tris(bromomethyl)benzene, especially 1,3,5-Tris(bromomethyl)benzene (TBMB), or a derivative thereof.

In one embodiment, the molecular scaffold is 2,4,6-Tris(bromomethyl)mesitylene. It is similar to 1,3,5-Tris(bromomethyl)benzene but contains additionally three methyl groups attached to the benzene ring. This has the advantage that the additional methyl groups may form further contacts with the polypeptide and hence add additional structural constraint.

The molecular scaffold of the invention contains chemical groups that allow functional groups of the polypeptide of the encoded library of the invention to form covalent links with the molecular scaffold. Said chemical groups are selected from a wide range of functionalities including amines, thiols, alcohols, ketones, aldehydes, nitriles, carboxylic acids, esters, alkenes, alkynes, anhydrides, succinimides, maleimides, azides, alkyl halides and acyl halides.

(ii) Polypeptide

The reactive groups of the polypeptides can be provided by side chains of natural or non-natural amino acids. The reactive groups of the polypeptides can be selected from thiol groups, amino groups, carboxyl groups, guanidinium groups, phenolic groups or hydroxyl groups. The reactive groups of the polypeptides can be selected from azide, keto-carbonyl, alkyne, vinyl, or aryl halide groups. The reactive groups of the polypeptides for linking to a molecular scaffold can be the amino or carboxy termini of the polypeptide.

In some embodiments each of the reactive groups of the polypeptide for linking to a molecular scaffold are of the same type. For example, each reactive group may be a cysteine residue. Further details are provided in WO2009098450.

In some embodiments the reactive groups for linking to a molecular scaffold may comprise two or more different types, or may comprise three or more different types. For example, the reactive groups may comprise two cysteine residues and one lysine residue, or may comprise one cysteine residue, one lysine residue and one N-terminal amine.

Cysteine can be employed because it has the advantage that its reactivity is most different from all other amino acids. Scaffold reactive groups that could be used on the molecular scaffold to react with thiol groups of cysteines are alkyl halides (or also named halogenoalkanes or haloalkanes). Examples are bromomethylbenzene (the scaffold reactive group exemplified by TBMB) or iodoacetamide. Other scaffold reactive groups that are used to couple selectively compounds to cysteines in proteins are maleimides. Examples of maleimides which may be used as molecular scaffolds in the invention include: tris-(2-maleimidoethyl)amine, tris-(2-maleimidoethyl)benzene, tris-(maleimido)benzene. Selenocysteine is also a natural amino acid which has a similar reactivity to cysteine and can be used for the same reactions. Thus, wherever cysteine is mentioned, it is typically acceptable to substitute selenocysteine unless the context suggests otherwise.

Lysines (and primary amines of the N-terminus of peptides) are also suited as reactive groups to modify peptides on phage by linking to a molecular scaffold. However, they are more abundant in phage proteins than cysteines and there is a higher risk that phage particles might become crosslinked or that they might lose their infectivity. Nevertheless, it has been found that lysines are especially useful in intramolecular reactions (e.g. when a molecular scaffold is already linked to the phage peptide) to form a second or consecutive linkage with the molecular scaffold. In this case the molecular scaffold reacts preferentially with lysines of the displayed peptide (in particular lysines that are in close proximity). Scaffold reactive groups that react selectively with primary amines are succinimides, aldehydes or alkyl halides. In the bromomethyl group that is used in a number of the accompanying examples, the electrons of the benzene ring can stabilize the cationic transition state. This particular aryl halide is therefore 100-1000 times more reactive than alkyl halides. Examples of succinimides for use as molecular scaffold include tris-(succinimidyl aminotriacetate), 1,3,5-Benzenetriacetic acid. Examples of aldehydes for use as molecular scaffold include Triformylmethane. Examples of alkyl halides for use as molecular scaffold include 1,3,5-Tris(bromomethyl)-2,4,6-trimethylbenzene, 1,3,5-Tris(bromomethyl)benzene, 1,3,5-Tris(bromomethyl)-2,4,6-triethylbenzene.

The amino acids with reactive groups for linking to a molecular scaffold may be located at any suitable positions within the polypeptide. In order to influence the particular structures or loops created, the positions of the amino acids having the reactive groups may be varied by the skilled operator, e.g. by manipulation of the nucleic acid encoding the polypeptide in order to mutate the polypeptide produced. By such means, loop length can be manipulated in accordance with the present teaching.

For example, the polypeptide can comprise the sequence $AC(X)_nC(X)_mCG$, wherein X stands for a random natural amino acid, A for alanine, C for cysteine and G for glycine and n and m, which may be the same or different, are numbers between 3 and 6.

(iii) Reactive Groups of the Polypeptide

The molecular scaffold of the invention may be bonded to the polypeptide via functional or reactive groups on the polypeptide. These are typically formed from the side chains of particular amino acids found in the polypeptide polymer. Such reactive groups may be a cysteine side chain, a lysine side chain, or an N-terminal amine group or any other suitable reactive group. Again, details may be found in WO2009098450.

Examples of reactive groups of natural amino acids are the thiol group of cysteine, the amino group of lysine, the carboxyl group of aspartate or glutamate, the guanidinium group of arginine, the phenolic group of tyrosine or the hydroxyl group of serine. Non-natural amino acids can provide a wide range of reactive groups including an azide, a keto-carbonyl, an alkyne, a vinyl, or an aryl halide group. The amino and carboxyl group of the termini of the polypeptide can also serve as reactive groups to form covalent bonds to a molecular scaffold/molecular core.

The polypeptides of the invention contain at least three reactive groups. Said polypeptides can also contain four or more reactive groups. The more reactive groups are used, the more loops can be formed in the molecular scaffold.

In a preferred embodiment, polypeptides with three reactive groups are generated. Reaction of said polypeptides with a molecular scaffold/molecular core having a three-fold rotational symmetry generates a single product isomer. The generation of a single product isomer is favourable for several reasons. The nucleic acids of the compound libraries encode only the primary sequences of the polypeptide but not the isomeric state of the molecules that are formed upon reaction of the polypeptide with the molecular core. If only one product isomer can be formed, the assignment of the nucleic acid to the product isomer is clearly defined. If multiple product isomers are formed, the nucleic acid can not give information about the nature of the product isomer that was isolated in a screening or selection process. The formation of a single product isomer is also advantageous if a specific member of a library of the invention is synthesized. In this case, the chemical reaction of the polypeptide with the molecular scaffold yields a single product isomer rather than a mixture of isomers.

In another embodiment of the invention, polypeptides with four reactive groups are generated. Reaction of said polypeptides with a molecular scaffold/molecular core having a tetrahedral symmetry generates two product isomers. Even though the two different product isomers are encoded by one and the same nucleic acid, the isomeric nature of the isolated isomer can be determined by chemically synthesizing both isomers, separating the two isomers and testing both isomers for binding to a target ligand.

In one embodiment of the invention, at least one of the reactive groups of the polypeptides is orthogonal to the remaining reactive groups. The use of orthogonal reactive groups allows the directing of said orthogonal reactive groups to specific sites of the molecular core. Linking strategies involving orthogonal reactive groups may be used to limit the number of product isomers formed. In other words, by choosing distinct or different reactive groups for one or more of the at least three bonds to those chosen for the remainder of the at least three bonds, a particular order of bonding or directing of specific reactive groups of the polypeptide to specific positions on the molecular scaffold may be usefully achieved.

In another embodiment, the reactive groups of the polypeptide of the invention are reacted with molecular linkers wherein said linkers are capable to react with a molecular scaffold so that the linker will intervene between the molecular scaffold and the polypeptide in the final bonded state.

In some embodiments, amino acids of the members of the libraries or sets of polypeptides can be replaced by any natural or non-natural amino acid. Excluded from these exchangeable amino acids are the ones harbouring functional groups for cross-linking the polypeptides to a molecular core, such that the loop sequences alone are exchangeable. The exchangeable polypeptide sequences have either random sequences, constant sequences or sequences with random and constant amino acids. The amino acids with reactive groups are either located in defined positions within the polypeptide, since the position of these amino acids determines loop size.

Replacement of the amino acids in the loops of the polypeptides with non-natural amino acids can improve the plasma residence time of polypeptide ligands, by increasing their resistance to protease degradation. Suitable amino acid modifications can include methylated amino acids, hydroxyl amino acids, guanidyl amino acids, and the like. Methods are known in the art, such as N-methyl scanning, which can be used to identify residues which are suitable for replacement to endow protease resistance.

In one embodiment, an polypeptide with three reactive groups has the sequence $(X)_l Y(X)_m Y(X)_n Y(X)_o$, wherein Y represents an amino acid with a reactive group, X represents a random amino acid, m and n are numbers between 3 and 6 defining the length of intervening polypeptide segments, which may be the same or different, and l and o are numbers between 0 and 20 defining the length of flanking polypeptide segments.

Alternatives to thiol-mediated conjugations can be used to attach the molecular scaffold to the peptide via covalent interactions. Alternatively these techniques may be used in modification or attachment of further moieties (such as small molecules of interest which are distinct from the molecular scaffold) to the polypeptide after they have been selected or isolated according to the present invention—in this embodiment then clearly the attachment need not be covalent and may embrace non-covalent attachment. These methods may be used instead of (or in combination with) the thiol mediated methods by producing phage that display proteins and peptides bearing unnatural amino acids with the requisite chemical reactive groups, in combination small molecules that bear the complementary reactive group, or by incorporating the unnatural amino acids into a chemically or recombinantly synthesised polypeptide when the molecule is being made after the selection/isolation phase. Further details can be found in WO2009098450 or Heinis, et al., *Nat Chem Biol* 2009, 5 (7), 502-7.

(iv) Combination of Loops to Form Multispecific Molecules

Loops from peptide ligands, or repertoires of peptide ligands, are advantageously combined by sequencing and de novo synthesis of a polypeptide incorporating the combined loops. Alternatively, nucleic acids encoding such polypeptides can be synthesised.

Where repertoires are to be combined, particularly single loop repertoires, the nucleic acids encoding the repertoires are advantageously digested and re-ligated, to form a novel repertoire having different combinations of loops from the constituent repertoires. Phage vectors can include polylinkers and other sites for restriction enzymes which can provide unique points for cutting and relegation the vectors, to create the desired multispecific peptide ligands. Methods for manipulating phage libraries are well known in respect of antibodies, and can be applied in the present case also.

(v) Attachment of Effector Groups and Functional Groups

Effector and/or functional groups can be attached, for example, to the N or C termini of the polypeptide, or to the molecular scaffold.

Appropriate effector groups include antibodies and parts or fragments thereof. For instance, an effector group can include an antibody light chain constant region (CL), an antibody CH1 heavy chain domain, an antibody CH2 heavy chain domain, an antibody CH3 heavy chain domain, or any combination thereof, in addition to the one or more constant region domains. An effector group may also comprise a hinge region of an antibody (such a region normally being found between the CH1 and CH2 domains of an IgG molecule).

In a further preferred embodiment of this aspect of the invention, an effector group according to the present invention is an Fc region of an IgG molecule. Advantageously, a peptide ligand-effector group according to the present invention comprises or consists of a peptide ligand Fc fusion having a tβ half-life of a day or more, two days or more, 3 days or more, 4 days or more, 5 days or more, 6 days or more or 7 days or more. Most advantageously, the peptide ligand according to the present invention comprises or consists of a peptide ligand Fc fusion having a tβ half-life of a day or more.

Functional groups include, in general, binding groups, drugs, reactive groups for the attachment of other entities, functional groups which aid uptake of the macrocyclic peptides into cells, and the like.

The ability of peptides to penetrate into cells will allow peptides against intracellular targets to be effective. Targets that can be accessed by peptides with the ability to penetrate into cells include transcription factors, intracellular signalling molecules such as tyrosine kinases and molecules involved in the apoptotic pathway. Functional groups which enable the penetration of cells include peptides or chemical groups which have been added either to the peptide or the molecular scaffold. Peptides such as those derived from such as VP22, HIV-Tat, a homeobox protein of Drosophila (Antennapedia), e.g. as described in Chen and Harrison, Biochemical Society Transactions (2007) Volume 35, part 4, p 821 "Cell-penetrating peptides in drug development: enabling intracellular targets" and "Intracellular delivery of large molecules and small peptides by cell penetrating peptides" by Gupta et al. in Advanced Drug Discovery Reviews (2004) Volume 57 9637. Examples of short peptides which have been shown to be efficient at translocation through plasma membranes include the 16 amino acid penetratin peptide from Drosophila Antennapedia protein (Derossi et al (1994) J Biol. Chem. Volume 269 p 10444 "The third helix of the Antennapedia homeodomain translocates through biological membranes"), the 18 amino acid 'model amphipathic peptide' (Oehlke et al (1998) Biochim Biophys Acts Volume 1414 p 127 "Cellular uptake of an alpha-helical amphipathic model peptide with the potential to deliver polar compounds into the cell interior non-endocytically") and arginine rich regions of the HIV TAT protein. Non peptidic approaches include the use of small molecule mimics or SMOCs that can be easily attached to biomolecules (Okuyama et al (2007) Nature Methods Volume 4 p 153 'Small-molecule mimics of an a-helix for efficient transport of proteins into cells'. Other chemical strategies to add guanidinium groups to molecules also enhance cell penetration (Elson-Scwab et al (2007) J Biol Chem Volume 282 p 13585 "Guanidinylated Neomcyin Delivers Large Bioactive Cargo into cells through a heparin Sulphate Dependent Pathway"). Small molecular weight molecules such as steroids may be added to the molecular scaffold to enhance uptake into cells.

One class of functional groups which may be attached to peptide ligands includes antibodies and binding fragments thereof, such as Fab, Fv or single domain fragments. In particular, antibodies which bind to proteins capable of increasing the half-life of the peptide ligand in vivo may be used.

RGD peptides, which bind to integrins which are present on many cells, may also be incorporated.

In one embodiment, a peptide ligand-effector group according to the invention has a tβ half-life selected from the group consisting of: 12 hours or more, 24 hours or more, 2 days or more, 3 days or more, 4 days or more, 5 days or more, 6 days or more, 7 days or more, 8 days or more, 9 days or more, 10 days or more, 11 days or more, 12 days or more, 13 days or more, 14 days or more, 15 days or more or 20 days or more. Advantageously a peptide ligand-effector group or composition according to the invention will have a tβ half-life in the range 12 to 60 hours. In a further embodiment, it will have a tβ half-life of a day or more. In a further embodiment still, it will be in the range 12 to 26 hours.

Functional groups include drugs, such as cytotoxic agents for cancer therapy. These include Alkylating agents such as Cisplatin and carboplatin, as well as oxaliplatin, mechlorethamine, cyclophosphamide, chlorambucil, ifosfamide; Anti-metabolites including purine analogs azathioprine and mercaptopurine)) or pyrimidine analogs; plant alkaloids and terpenoids including vinca alkaloids such as Vincristine, Vinblastine, Vinorelbine and Vindesine; Podophyllotoxin and its derivatives etoposide and teniposide; Taxanes, including paclitaxel, originally known as Taxol; topoisomerase inhibitors including camptothecins: irinotecan and topotecan, and type II inhibitors including amsacrine, etoposide, etoposide phosphate, and teniposide. Further agents can include Antitumour antibiotics which include the immunosuppressant dactinomycin (which is used in kidney transplantations), doxorubicin, epirubicin, bleomycin and others.

Possible effector groups also include enzymes, for instance such as carboxypeptidase G2 for use in enzyme/prodrug therapy, where the peptide ligand replaces antibodies in ADEPT.

(vi) Synthesis

It should be noted that once a polypeptide of interest is isolated or identified according to the present invention, then its subsequent synthesis may be simplified wherever possible.

Thus, groups or sets of polypeptides need not be produced by recombinant DNA techniques. For example, the sequence of polypeptides of interest may be determined, and they may be manufactured synthetically by standard techniques followed by reaction with a molecular scaffold in vitro. When this is performed, standard chemistry may be used since there is no longer any need to preserve the functionality or integrity of the genetically encoded carrier particle, such as phage. This enables the rapid large scale preparation of soluble material for further downstream experiments or validation. In this regard, large scale preparation of the candidates or leads identified by the methods of the present invention could be accomplished using conventional chemistry such as that disclosed in Timmerman et al.

Thus, the invention also relates to manufacture of polypeptides or conjugates selected as set out herein, wherein the manufacture comprises optional further steps as explained below. In one embodiment, these steps are carried out on the end product polypeptide/conjugate made by chemical synthesis, rather than on the phage.

Optionally amino acid residues in the polypeptide of interest may be substituted when manufacturing a conjugate or complex e.g. after the initial isolation/identification step.

Peptides can also be extended, to incorporate for example another loop and therefore introduce multiple specificities.

To extend the peptide, it may simply be extended chemically at its N-terminus or C-terminus using standard solid phase or solution phase chemistry. Standard protein chemistry may be used to introduce an activatable N- or C-terminus. Alternatively additions may be made by fragment condensation or native chemical ligation e.g. as described in (Dawson P E, Muir T W, Clark-Lewis I, Kent, S B H. 1994. Synthesis of Proteins by Native Chemical Ligation. Science 266:776-779), or by enzymes, for example using subtiligase as described in (Subtiligase: a tool for semisynthesis of proteins Chang T K, Jackson D Y, Burnier J P, Wells J A Proc Natl Acad Sci USA. 1994 Dec. 20; 91(26):12544-8 or in Bioorganic & Medicinal Chemistry Letters Tags for labelling protein N-termini with subtiligase for proteomics Volume 18, Issue 22, 15 Nov. 2008, Pages 6000-6003 Tags for labeling protein N-termini with subtiligase for proteomics; Hikari A. I. Yoshihara, Sami Mahrus and James A. Wells).

Alternatively, the peptides may be extended or modified by further conjugation through disulphide bonds. This has the additional advantage of allowing the first and second peptide to dissociate from each other once within the reducing environment of the cell. In this case, the molecular scaffold (eg. TBMB) could be added during the chemical synthesis of the first peptide so as to react with the three cysteine groups; a further cysteine could then be appended to the N-terminus of the first peptide, so that this cysteine only reacted with a free cysteine of the second peptide.

Similar techniques apply equally to the synthesis/coupling of two bicyclic and bispecific macrocycles, potentially creating a tetraspecific molecule.

Furthermore, addition of other functional groups or effector groups may be accomplished in the same manner, using appropriate chemistry, coupling at the N- or C-termini or via side chains. In one embodiment, the coupling is conducted in such a manner that it does not block the activity of either entity.

(B) Repertoires, Sets and Groups of Polypeptide Ligands
(i) Construction of Libraries Libraries intended for selection may be constructed using techniques known in the art, for example as set forth in WO2004/077062, or biological systems, including phage vector systems as described herein. Other vector systems are known in the art, and include other phage (for instance, phage lambda), bacterial plasmid expression vectors, eukaryotic cell-based expression vectors, including yeast vectors, and the like. For example, see WO2009098450 or Heinis, et al., *Nat Chem Biol* 2009, 5 (7), 502-7.

Non-biological systems such as those set forth in WO2004/077062 are based on conventional chemical screening approaches. They are simple, but lack the power of biological systems since it is impossible, or at least impracticably onerous, to screen large libraries of peptide ligands. However, they are useful where, for instance, only a small number of peptide ligands needs to be screened. Screening by such individual assays, however, may be time-consuming and the number of unique molecules that can be tested for binding to a specific target generally does not exceed $10^6$ chemical entities.

In contrast, biological screening or selection methods generally allow the sampling of a much larger number of different molecules. Thus biological methods can be used in application of the invention. In biological procedures, molecules are assayed in a single reaction vessel and the ones with favourable properties (i.e. binding) are physically separated from inactive molecules. Selection strategies are available that allow to generate and assay simultaneously more than $10^{13}$ individual compounds. Examples for powerful affinity selection techniques are phage display, ribosome display, mRNA display, yeast display, bacterial display or RNA/DNA aptamer methods. These biological in vitro selection methods have in common that ligand repertoires are encoded by DNA or RNA. They allow the propagation and the identification of selected ligands by sequencing. Phage display technology has for example been used for the isolation of antibodies with very high binding affinities to virtually any target.

When using a biological system, once a vector system is chosen and one or more nucleic acid sequences encoding polypeptides of interest are cloned into the library vector, one may generate diversity within the cloned molecules by undertaking mutagenesis prior to expression; alternatively, the encoded proteins may be expressed and selected before mutagenesis and additional rounds of selection are performed.

Mutagenesis of nucleic acid sequences encoding structurally optimised polypeptides is carried out by standard molecular methods. Of particular use is the polymerase chain reaction, or PCR, (Mullis and Faloona (1987) Methods Enzymol., 155: 335, herein incorporated by reference). PCR, which uses multiple cycles of DNA replication catalysed by a thermostable, DNA-dependent DNA polymerase to amplify the target sequence of interest, is well known in the art. The construction of various antibody libraries has been discussed in Winter et al. (1994) Ann. Rev. Immunology 12, 433-55, and references cited therein.

Alternatively, given the short chain lengths of the polypeptides according to the invention, the variants are preferably synthesised de novo and inserted into suitable expression vectors. Peptide synthesis can be carried out by standard techniques known in the art, as described above. Automated peptide synthesisers are widely available, such as the Applied Biosystems ABI 433 (Applied Biosystems, Foster City, Calif., USA)

(ii) Genetically Encoded Diversity

In one embodiment, the polypeptides of interest are genetically encoded. This offers the advantage of enhanced diversity together with ease of handling. An example of a genetically polypeptide library is a mRNA display library. Another example is a replicable genetic display package (rgdp) library such as a phage display library. In one embodiment, the polypeptides of interest are genetically encoded as a phage display library.

Thus, in one embodiment the complex of the invention comprises a replicable genetic display package (rgdp) such as a phage particle. In these embodiments, the nucleic acid can be comprised by the phage genome. In these embodiments, the polypeptide can be comprised by the phage coat.

In some embodiments, the invention may be used to produce a genetically encoded combinatorial library of polypeptides which are generated by translating a number of nucleic acids into corresponding polypeptides and linking molecules of said molecular scaffold to said polypeptides.

The genetically encoded combinatorial library of polypeptides may be generated by phage display, yeast display, ribosome display, bacterial display or mRNA display.

Techniques and methodology for performing phage display can be found in WO2009098450.

In one embodiment, screening may be performed by contacting a library, set or group of polypeptide ligands with a target and isolating one or more member(s) that bind to said target.

In another embodiment, individual members of said library, set or group are contacted with a target in a screen and members of said library that bind to said target are identified.

In another embodiment, members of said library, set or group are simultaneously contacted with a target and members that bind to said target are selected.

The target(s) may be a peptide, a protein, a polysaccharide, a lipid, a DNA or a RNA.

The target may be a receptor, a receptor ligand, an enzyme, a hormone or a cytokine.

The target may be a prokaryotic protein, a eukaryotic protein, or an archeal protein. More specifically the target ligand may be a mammalian protein or an insect protein or a bacterial protein or a fungal protein or a viral protein.

The target ligand may be an enzyme, such as a protease.

It should be noted that the invention also embraces polypeptide ligands isolated from a screen according to the invention. In one embodiment the screening method(s) of the invention further comprise the step of: manufacturing a quantity of the polypeptide isolated as capable of binding to said targets.

The invention also relates to peptide ligands having more than two loops. For example, tricyclic polypeptides joined to a molecular scaffold can be created by joining the N- and C-termini of a bicyclic polypeptide joined to a molecular scaffold according to the present invention. In this manner, the joined N and C termini create a third loop, making a tricyclic polypeptide. This embodiment need not be carried out on phage, but can be carried out on a polypeptide-molecular scaffold conjugate as described herein. Joining the N- and C-termini is a matter of routine peptide chemistry. In case any guidance is needed, the C-terminus may be activated and/or the N- and C-termini may be extended for example to add a cysteine to each end and then join them by disulphide bonding. Alternatively the joining may be accomplished by use of a linker region incorporated into the N/C termini. Alternatively the N and C termini may be joined by a conventional peptide bond. Alternatively any other suitable means for joining the N and C termini may be employed, for example N—C-cyclization could be done by standard techniques, for example as disclosed in Linde et al. Peptide Science 90, 671-682 (2008) "Structure-activity relationship and metabolic stability studies of backbone cyclization and N-methylation of melanocortin peptides", or as in Hess et al. J. Med. Chem. 51, 1026-1034 (2008) "backbone cyclic peptidomimetic melanocortin-4 receptor agonist as a novel orally administered drug lead for treating obesity". One advantage of such tricyclic molecules is the avoidance of proteolytic degradation of the free ends, in particular by exoprotease action. Another advantage of a tricyclic polypeptide of this nature is that the third loop may be utilised for generally applicable functions such as BSA binding, cell entry or transportation effects, tagging or any other such use. It will be noted that this third loop will not typically be available for selection (because it is not produced on the phage but only on the polypeptide-molecular scaffold conjugate) and so its use for other such biological functions still advantageously leaves both loops 1 and 2 for selection/creation of specificity.

(iii) Phage Purification

Any suitable means for purification of the phage may be used. Standard techniques may be applied in the present invention. For example, phage may be purified by filtration or by precipitation such as PEG precipitation; phage particles may be produced and purified by polyethylene-glycol (PEG) precipitation as described previously. Details can be found in WO2009098450.

In case further guidance is needed, reference is made to Jespers et al (Protein Engineering Design and Selection 2004 17(10):709-713. Selection of optical biosensors from chemisynthetic antibody libraries.) In one embodiment phage may be purified as taught therein. The text of this publication is specifically incorporated herein by reference for the method of phage purification; in particular reference is made to the materials and methods section starting part way down the right-column at page 709 of Jespers et al.

Moreover, the phage may be purified as published by Marks et al J. Mol. Biol vol 222 pp 581-597, which is specifically incorporated herein by reference for the particular description of how the phage production/purification is carried out.

(iv) Reaction Chemistry

The present invention makes use of chemical conditions for the modification of polypeptides which advantageously retain the function and integrity of the genetically encoded element of the product. Specifically, when the genetically encoded element is a polypeptide displayed on the surface of a phage encoding it, the chemistry advantageously does not compromise the biological integrity of the phage. In general, conditions are set out in WO2009098450.

(C) Use of Polypeptide Ligands According to the Invention

Polypeptide ligands selected according to the method of the present invention may be employed in in vivo therapeutic and prophylactic applications, in vitro and in vivo diagnostic applications, in vitro assay and reagent applications, and the like. Ligands having selected levels of specificity are useful in applications which involve testing in non-human animals, where cross-reactivity is desirable, or in diagnostic applications, where cross-reactivity with homologues or paralogues needs to be carefully controlled. In some applications, such as vaccine applications, the ability to elicit an immune response to predetermined ranges of antigens can be exploited to tailor a vaccine to specific diseases and pathogens.

Substantially pure peptide ligands of at least 90 to 95% homogeneity are preferred for administration to a mammal, and 98 to 99% or more homogeneity is most preferred for pharmaceutical uses, especially when the mammal is a human. Once purified, partially or to homogeneity as desired, the selected polypeptides may be used diagnostically or therapeutically (including extracorporeally) or in developing and performing assay procedures, immunofluorescent stainings and the like (Lefkovite and Pernis, (1979 and 1981) Immunological Methods, Volumes I and II, Academic Press, NY).

The peptide ligands of the present invention will typically find use in preventing, suppressing or treating inflammatory states, allergic hypersensitivity, cancer, bacterial or viral infection, and autoimmune disorders (which include, but are not limited to, Type I diabetes, multiple sclerosis, rheumatoid arthritis, systemic lupus erythematosus, Crohn's disease and myasthenia gravis).

In the instant application, the term "prevention" involves administration of the protective composition prior to the induction of the disease. "Suppression" refers to administration of the composition after an inductive event, but prior to the clinical appearance of the disease. "Treatment" involves administration of the protective composition after disease symptoms become manifest.

Animal model systems which can be used to screen the effectiveness of the peptide ligands in protecting against or treating the disease are available. The use of animal model systems is facilitated by the present invention, which allows the development of polypeptide ligands which can cross react with human and animal targets, to allow the use of animal models.

Methods for the testing of systemic lupus erythematosus (SLE) in susceptible mice are known in the art (Knight et al. (1978) J Exp. Med., 147: 1653; Reinersten et al. (1978) New Eng. J: Med., 299: 515). Myasthenia Gravis (MG) is tested in SJL/J female mice by inducing the disease with soluble AchR protein from another species (Lindstrom et al. (1988) Adv. Inzn7unol., 42: 233). Arthritis is induced in a susceptible strain of mice by injection of Type II collagen (Stuart et al. (1984) Ann. Rev. Immunol., 42: 233). A model by which adjuvant arthritis is induced in susceptible rats by injection of mycobacterial heat shock protein has been described (Van Eden et al. (1988) Nature, 331: 171). Thyroiditis is induced in mice by administration of thyroglobulin as described (Maron et al. (1980) J. Exp. Med., 152: 1115). Insulin dependent diabetes mellitus (IDDM) occurs naturally or can be induced in certain strains of mice such as those described by Kanasawa et al. (1984) Diabetologia, 27: 113. EAE in mouse and rat serves as a model for MS in human. In this model, the demyelinating disease is induced by administration of myelin basic protein (see Paterson (1986) Textbook of Immunopathology, Mischer et al., eds., Grune and Stratton, New York, pp. 179-213; McFarlin et al. (1973) Science, 179: 478: and Satoh et al. (1987) J; Immunol., 138: 179).

Generally, the present peptide ligands will be utilised in purified form together with pharmacologically appropriate carriers. Typically, these carriers include aqueous or alcoholic/aqueous solutions, emulsions or suspensions, any including saline and/or buffered media. Parenteral vehicles include sodium chloride solution, Ringer's dextrose, dextrose and sodium chloride and lactated Ringer's. Suitable physiologically-acceptable adjuvants, if necessary to keep a polypeptide complex in suspension, may be chosen from thickeners such as carboxymethylcellulose, polyvinylpyrrolidone, gelatin and alginates.

Intravenous vehicles include fluid and nutrient replenishers and electrolyte replenishers, such as those based on Ringer's dextrose. Preservatives and other additives, such as antimicrobials, antioxidants, chelating agents and inert gases, may also be present (Mack (1982) Remington's Pharmaceutical Sciences, 16th Edition).

The peptide ligands of the present invention may be used as separately administered compositions or in conjunction with other agents. These can include antibodies, antibody fragments and various immunotherapeutic drugs, such as cyclosporine, methotrexate, adriamycin or cisplatinum, and immunotoxins. Pharmaceutical compositions can include "cocktails" of various cytotoxic or other agents in conjunction with the selected antibodies, receptors or binding proteins thereof of the present invention, or even combinations of selected polypeptides according to the present invention having different specificities, such as polypeptides selected using different target ligands, whether or not they are pooled prior to administration.

The route of administration of pharmaceutical compositions according to the invention may be any of those commonly known to those of ordinary skill in the art. For therapy, including without limitation immunotherapy, the selected antibodies, receptors or binding proteins thereof of the invention can be administered to any patient in accordance with standard techniques. The administration can be by any appropriate mode, including parenterally, intravenously, intramuscularly, intraperitoneally, transdermally, via the pulmonary route, or also, appropriately, by direct infusion with a catheter. The dosage and frequency of administration will depend on the age, sex and condition of the patient, concurrent administration of other drugs, counter-indications and other parameters to be taken into account by the clinician.

The peptide ligands of this invention can be lyophilised for storage and reconstituted in a suitable carrier prior to use. This technique has been shown to be effective and art-known lyophilisation and reconstitution techniques can be employed. It will be appreciated by those skilled in the art that lyophilisation and reconstitution can lead to varying degrees of activity loss and that use levels may have to be adjusted upward to compensate.

The compositions containing the present peptide ligands or a cocktail thereof can be administered for prophylactic and/or therapeutic treatments. In certain therapeutic applications, an adequate amount to accomplish at least partial inhibition, suppression, modulation, killing, or some other measurable parameter, of a population of selected cells is defined as a "therapeutically-effective dose". Amounts needed to achieve this dosage will depend upon the severity of the disease and the general state of the patient's own immune system, but generally range from 0.005 to 5.0 mg of selected peptide ligand per kilogram of body weight, with doses of 0.05 to 2.0 mg/kg/dose being more commonly used. For prophylactic applications, compositions containing the present peptide ligands or cocktails thereof may also be administered in similar or slightly lower dosages.

A composition containing a peptide ligand according to the present invention may be utilised in prophylactic and therapeutic settings to aid in the alteration, inactivation, killing or removal of a select target cell population in a mammal. In addition, the selected repertoires of polypeptides described herein may be used extracorporeally or in vitro selectively to kill, deplete or otherwise effectively remove a target cell population from a heterogeneous collection of cells. Blood from a mammal may be combined extracorporeally with the selected peptide ligands whereby the undesired cells are killed or otherwise removed from the blood for return to the mammal in accordance with standard techniques.

(D) Mutation of Polypeptides

The desired diversity is typically generated by varying the selected molecule at one or more positions. The positions to be changed are selected, such that libraries are constructed for each individual position in the loop sequences. Where appropriate, one ore more positions may be omitted from the selection procedure, for instance if it becomes apparent that those positions are not available for mutation without loss of activity.

The variation can then be achieved either by randomisation, during which the resident amino acid is replaced by any amino acid or analogue thereof, natural or synthetic, producing a very large number of variants or by replacing the resident amino acid with one or more of a defined subset of amino acids, producing a more limited number of variants.

Various methods have been reported for introducing such diversity. Methods for mutating selected positions are also well known in the art and include the use of mismatched oligonucleotides or degenerate oligonucleotides, with or without the use of PCR. For example, several synthetic antibody libraries have been created by targeting mutations to the antigen binding loops. The same techniques could be used in the context of the present invention. For example, the H3 region of a human tetanus toxoid-binding Fab has been randomised to create a range of new binding specificities (Barbas et al. (1992) Proc. Natl. Acad. Sci. USA, 89: 4457). Random or semi-random H3 and L3 regions have been appended to germline V gene segments to produce large libraries with mutated framework regions (Hoogenboom- & Winter (1992) R Mol. Biol., 227: 381; Barbas et al. (1992) Proc. Natl. Acad. Sci. USA, 89: 4457; Nissim et al. (1994) EMBO J, 13: 692; Griffiths et al. (1994) EMBO J, 13: 3245; De Kruif et al. (1995) J. Mol. Biol., 248: 97). Such diversification has been extended to include some or all of the other antigen binding loops (Crameri et al. (1996) Nature Med., 2: 100; Riechmann et al. (1995) BiolTechnology, 13: 475; Morphosys, WO97/08320, supra).

However, since the polypeptides used in the present invention are much smaller than antibodies, the preferred method is to synthesise mutant polypeptides de novo. Mutagenesis of structured polypeptides is described above, in connection with library construction.

The invention is further described below with reference to the following examples.

EXAMPLES

Materials and Methods
Cloning of Phage Libraries

Phage libraries were generated according to Heinis et al., *Nat Chem Biol* 2009, 5 (7), 502-7). In Heinis et al, the genes encoding a semi-random peptide with the sequence Xaa-Cys-(Xaa)$_3$-Cys-(Xaa)$_3$-, the linker Gly-Gly-Ser-Gly [SEQ ID No. 2] and the two disulfide-free domains D1 and D2 (Kather, et al., *J Mol Biol* 2005, 354 (3), 666-78) were cloned in the correct orientation into the phage vector fd0D12 to obtain 'library 3×3'. The genes encoding the peptide repertoire and the two gene 3 domains were stepwise created in two consecutive PCR reactions. First, the genes of D1 and D2 were PCR amplified with the two primer prepcr (5'-GGCGGTTCTGGCGCTGAAACTGTT-GAAAGTAG-3') [SEQ ID No. 3] and sfi2fo (5'-GAAGC-CATGGCCCCCGAGGCCCCGGACGGAGCATT-GACAGG-3' [SEQ ID No. 4]; restriction site is underlined) using the vector fdg3p0ss21 (Kather, et al., *J Mol Biol* 2005, 354 (3), 666-78) as a template. Second, the DNA encoding the random peptides was appended in a PCR reaction using the primer sficx3ba: 5'-ATGCGGCCCAGCCGGCCATG-GCANNKTGTNNKNNKNNKTGCNNKNN KNNKNNK-TGTNNKGGGCGGTTCTGGCGCTG-3' [SEQ ID No. 5] (restriction site is underlined), and sfi2fo. The ligation of 55 and 11 μg of SfiI-digested fd0D12 plasmid and PCR product yielded $5.6 \times 10^8$ colonies on 10 20×20 cm chloramphenicol (30 μg/ml) 2YT plates. Colonies were scraped off the plates with 2YT media, supplemented with 15% glycerol and stored at −80° C. Construction of the libraries described herein employed the same technique to generate the semi-random peptide Pro-Ala-Met-Ala-Cys-(Xaa)$_3$-Cys-(Xaa)$_3$-Cys [SEQ ID No. 6] for a 3×3 library for example, and therefore replaced the sficx3ba primer sequence with: 5'-TATGCGGCCCAGCCGGCCATGGCATGTNNKNN-KNNKTGCNNKN NKNNKTGTGGCGGTTCTG-GCGCTG-3' [SEQ ID No. 7]. Libraries with other loop lengths were generated following the same methodology.
Phage Selections Glycerol stocks of phage libraries were diluted to $OD_{600}=0.1$ in 500 ml 2YT/chloramphenicol (30 μg/ml) cultures and phage were produced at 30° C. over night (15-16 hrs). Phage were purified and chemically modified as described in Heinis, et al., *Nat Chem Biol* 2009, 5 (7), 502-7 Biotinylated hPK (3 μg) (IHPKA, from human plasma, Innovative Research, Novi, Mich., USA) was incubated with 50 μl pre-washed magnetic streptavidin beads (Dynal, M-280 from Invitrogen, Paisley, UK) for 10 minutes at RT. Beads were washed 3 times prior to blocking with 0.5 ml washing buffer (10 mM Tris-Cl, pH 7.4, 150 mM NaCl, 10 mM MgCl$_2$, 1 mM CaCl$_2$) containing 1% BSA and 0.1% Tween 20 for 30 minutes at RT with rotation. Chemically modified phage (typically $10^{10}$-$10^{11}$ t.u. dissolved in 2 ml washing buffer) were concomitantly blocked by addition of 1 ml washing buffer containing 3% BSA and 0.3% Tween 20. Blocked beads were then mixed with the blocked chemically modified phage and incubated for 30 minutes on a rotating wheel at RT. Beads were washed 8 times with washing buffer containing 0.1% Tween 20 and twice with washing buffer before incubation with 100 μl of 50 mM glycine, pH 2.2 for 5 minutes. Eluted phage were transferred to 50 μl of 1 M Tris-Cl, pH 8 for neutralization, incubated with 30 ml TG1 cells at $OD_{600}=0.4$ for 90 minutes at 37° C. and the cells were plated on large 2YT/chloramphenicol plates. One or two additional rounds of panning were performed using the same procedures. In the second round of selection, neutravidin-coated magnetic beads were used to prevent the enrichment of streptavidin-specific peptides. The neutravidin beads were prepared by reacting 0.8 mg neutravidin (Pierce, Rockford, Ill., USA) with 0.5 ml tosyl-activated magnetic beads (Dynal, M-280 from Invitrogen, Paisley, UK) according to the supplier's instructions.
Cloning and Expression of Human, Monkey and Rat PK The catalytic domain of human, monkey and rat PK was expressed in mammalian cells as an inactive precursor having a pro-peptide connected N-terminally via a proTEV cleavage site to the catalytic domain. The expression vector was cloned and the protein expressed, activated and purified as described as follows. Synthetic genes coding for a PK signal sequence, a polyhistidine tag, a proTEV cleavage site, mature catalytic domain of PK and a stop codon were purchased from Geneart (Regensburg, Germany) (Supplementary materials). Plasmid DNA containing the synthetic genes for human, monkey (*Macaca mulatta*) and rat PK was prepared and the gene transferred into the pEXPR-IBA42 mammalian expression vector (IBA Biotechnology, Göttingen, Germany) using the restriction enzyme pair XhoI and HindIII (Fermentas, Vilnius, Latvia) and T4 DNA ligase (Fermentas). The ligated plasmids were transformed into XL-1 blue electrocompetent cells (Stratagene, Santa Clara, USA) and plated onto 2YT agar plates containing ampicillin (10 μg/ml). DNA from the three expression vectors (termed mPK, rPK and hPK) was produced and the correct sequences confirmed by DNA sequencing (Macrogen, Seoul, South Korea).

The three orthologous plasma kallikreins were expressed in mammalian cells as follows. 50 ml of suspension-adapted HEK-293 cells were grown in serum-free ExCell 293 medium (SAFC Biosciences, St. Louis, Mo.) in the presence of 4 mM glutamine and the histone deacetylase inhibitor valproic acid (3.75 mM) in an orbitally shaken 100 ml flask at 180 rpm in an ISF-4-W incubator (Kühner AG, Birsfelden, Switzerland) at 37° C. in the presence of 5% $CO_2$. The embryonic kidney (HEK-293) cells at high cell density ($20 \times 10^6$ cells/ml) (Backliwal, et al. *Biotechnol Bioeng* 2008, 99 (3), 721-7) were transfected with the three plasmids (300 μg/ml) using linear polyethylenimine (PEI, Polysciences, Eppenheim, Germany). At the end of the 7-day production phase, cells were harvested by centrifugation at 2,500 rpm for 15 min at 4° C. Any additional cell debris was removed from the medium by filtration through 0.45 µm PES membranes (Filter-top 250 ml low protein binding TPP). The polyhistidine-tagged protein was purified by Ni-affinity chromatography using Ni-NTA resin, washing buffer (500 mM NaCl, 25 mM Na$_2$HPO$_4$, pH7.4) and elution buffer (500 mM NaCl, 25 mM Na$_2$HPO$_4$, pH 7.4, 500 mM imidazole). The protein was partially activated with (50 units) proTEV (Promega, Madison, Wis., USA) and additionally purified by Ni-affinity chromatography and gel filtration (PD10 column, 150 mM NaCl, 0.5 mM EDTA, 50 mM HEPES, pH 7).

Synthesis and Purification of Bicyclic Peptides

Peptide sequences are shown in Tables 1 and 2. Peptide synthesis was based on Fmoc chemistry, using a Symphony peptide synthesiser manufactured by Peptide Instruments. Standard Fmoc-amino acids were employed (Sigma, Merck), with the following side chain protecting groups: Arg(Pbf); Asn(Trt); Asp(OtBu); Cys(Trt); Glu(OtBu); Gln (Trt); His(Trt); Lys(Boc); Ser(tBu); Thr(tBu); Trp(Boc); Tyr(tBu) (Sigma). The coupling reagent was HCTU (Pepceuticals), diisopropylethylamine (DIPEA, Sigma) was employed as a base, and deprotection was achieved with 20% piperidine in DMF (AGTC). Syntheses were performed at 100 umole scale using 0.37 mmole/gr Fmoc-Rink amide AM resin (AGTC), Fmoc-amino acids were utilised at a four-fold excess, and base was at a four-fold excess with respect to the amino acids. Amino acids were dissolved at 0.2 M in DMF, HCTU at 0.4 M in DMF, and DIPEA at 1.6 M in N-methylpyrrolidone (Alfa Aesar). Coupling times were generally 30 minutes, and deprotection times 2×2.5 minutes. Fmoc-N-methylglycine (Fmoc-Sar-OH, Merck) was coupled for 1 hr, and deprotection and coupling times for the following residue were 20 min and 1 hr, respectively. After synthesis, the resin was washed with dichloromethane, and dried. Cleavage of side-chain protecting groups and from the support was effected using 10 mL of 95:2.5:2.5:2.5 v/v/v/w TFA/H2O/iPr3SiH/dithiothreitol for 3 hours. Following cleavage, the spent resin was removed by filtration, and the filtrate was added to 35 mL of diethylether that had been cooled at −80 deg C. Peptide pellet was centrifuged, the etheric supernatant discarded, and the peptide pellet washed with cold ether two more times. Peptides were then resolubilised in 5-10 mL acetonitrile-water and lyophilised. A small sample was removed for analysis of purity of the crude product by mass spectrometry (MALDI-TOF, Voyager DE from Applied Biosystems). Following lyophilisation, peptide powders were taken up in 10 mL 6 M guanidinium hydrochloride in H2O, supplemented with 0.5 mL of 1 M dithiothreitrol, and loaded onto a C8 Luna preparative HPLC column (Phenomenex). Solvents (H2O, acetonitrile) were acidified with 0.1% heptafluorobutyric acid. The gradient ranged from 30-70% acetonitrile in 15 minutes, at a flowrate of 15/20 mL/min, using a Gilson preparative HPLC system. Fractions containing pure linear peptide material (as identified by MALDI) were combined, and modified with trisbromomethylbenzene (TBMB, Sigma). For this, linear peptide was diluted with H$_2$O up to ~35 mL, ~500 uL of 100 mM TBMB in acetonitrile was added, and the reaction was initiated with 5 mL of 1 M NH4HCO3 in H2O. The reaction was allowed to proceed for ~30 −60 min at RT, and lyophilised once the reaction had completed (judged by MALDI). Following lyophilisation, the modified peptide was purified as above, while replacing the Luna C8 with a Gemini C18 column (Phenomenex), and changing the acid to 0.1% trifluoroacetic acid. Pure fractions containing the correct TMB-modified material were pooled, lyophilised and kept at −20 deg C for storage.

Non-natural amino acids were acquired from the sources set forth in Table 5.

Bulky or hindered amino acids (NMe-Ser, NMe-Trp, NorHar, 4PhenylPro, Agb, Agp, NMe-Arg, Pen, Tic, Aib, Hyp, NMe-Ala, NMe-Cys, 4,4-BPAI, 3,3-DPA, Dpg, 1 NAI, 2NAI, Aze, 4BenzylPro, Ind) were usually coupled for 1 hours (20 min deprotection), and 6 hrs for the residue that followed (20 min deprotection). HCTU was used as a coupling reagent as before. Scale was usually at 50 umole.

Enzyme Assays

Functional enzyme assays were conducted in 10 mM Tris HCl, 150 mM NaCl, 10 mM MgCl$_2$, 1 mM CaCl$_2$ and 1 mg/mL BSA (all Sigma UK) pH7.4 at 25° C. in solid black 96 well plates. Briefly 26.5 pM human plasma kallikrein (purchased from Stratech, UK) or 500 pM rat plasma kallikrein (expressed and purified in house) were incubated in the absence or presence of increasing concentrations of test peptide for 15 minutes before addition of the fluorogenic substrate Z-PheArg-AMC (Enzo Lifesciences UK) to a final assay concentration of 100 µM in 4% DMSO. Release of AMC was measured using a Pherastar FS (BMG Labtech), excitation 360 nm, emission 460 nm. The rate of the linear phase of the reaction, typically 5 to 45 minutes, was calculated in MARS data analysis software (BMG labtech). The rate was then used to calculate the IC$_{50}$ and K$_i$ in Prism (GraphPad). A four parameter inhibition non-linear regression equation was used to calculate the IC$_{50}$. The One site-fit K$_i$ equation used to calculate the K$_i$, constraining the K$_d$ to the K$_m$ for the substrate which is 150 µM.

Plasma Stability Profiling

Three methods were employed to assess the stability of bicycles (peptides conjugated to molecular scaffolds) in plasma.

Method 1:

A rapid plasma stability profiling assay was developed that employed mass spectrometric detection (MALDI-TOF, Voyager DE, Applied Biosystems) of the parent mass, until the time when the parent peptide mass was no longer observable. Specifically, 200 uM of peptide was incubated in the presence of 35% rat or human plasma (Sera labs, using citrate as anticoagulant) at 37 deg C, which was supplemented with 1×PBS (derived from a 10×PBS Stock, Sigma). At various time points (i.e. t=0, 3, 24 hrs, henceafter daily up to 10 days), 2 uL of sample was added to 18 uL of 30 mM ammonium bicarbonate in a 1:1 mixture of acetonitrile: H2O. Samples were frozen at −80 deg C until the time of analysis. For mass spectrometric analysis that determines the approximate detection window of the peptide, the acetonitrile:H$_2$O-diluted sample of a given time point was spotted directly (0.7 uL) onto the MALDI plate. Matrix (alpha-cyanocinnamic acid, Sigma, prepared as a saturated solution in 1:1 acetonitrile:water containing 0.1% trifluoroacetic acid) was layered over the sample (1 uL). At a similar laser intensity setting on the MALDI TOF, the time could then be determined until parent peptide was no longer detectable. It should be noted that this is a qualitative assay serves to detect relative changes in plasma stability.

Method 2:

To obtain stability data more rapidly, peptides were also assessed in 95% plasma. Here, PBS was omitted, and a 1 mM peptide stock (in DMSO) was directly diluted into plasma (i.e. 2.5 uL stock into 47.5 uL plasma), giving a final concentration of 50 uM. 5 uL samples were taken at appropriate time points and frozen at −80 deg C. For analysis, the samples were defrosted, mixed with 15 uL of 1:1 acetonitrile:methanol, and centrifuged at 13 k for 5 min. 5 uL of the peptide-containing supernatant was aspirated and mixed with 30 mM ammonium bicarbonate in a 1:1 mixture of acetonitrile:H$_2$O. 1 uL of this was then spotted on the MALDI plate and analysed as described above. As above, it should be noted that this is a qualitative assay serves to detect relative changes in plasma stability.

Method 3:

To obtain plasma stability quantitatively, peptide stock solutions (1 mM in DMSO) were shipped to Biofocus, UK, who performed the analysis. Peptides were diluted to 100 uM with water, and diluted 1:20 in plasma (5 uM final concentration, with the plasma at 95%), sampled as appropriate, precipitated as above, and quantified using a Waters Xevo TQ-MS.

Example 1: Selection of Peptides with Differing Loop Length

In inhibition assays with a large panel of serine proteases, we confirmed the high target specificity of the recently developed bicyclic peptide inhibitor PK15 as well as its poor activity towards murine PK. In an attempt to identify PK inhibitors with a lower specificity, which might cross-react with PK from other species, we screened phage libraries of varying sizes of bicyclic peptides. This approach was challenging since some paralogous human serine proteases (e.g. hfXIa) are no more different in their amino acid sequences from hPK than murine PK differs from hPK (e.g. hfXIa and rPK both share 69% sequence identity with hPK) (Table 2 and FIG. 2).

Genetically encoded combinatorial libraries of bicyclic peptides were produced by displaying linear peptides of the format Cys-(Xaa)$_n$-Cys-(Xaa)$_n$-Cys (n=number of random amino acids Xaa) on phage and subsequent chemical cyclisation of the three cysteine side chains with tris-(bromomethly)benzene (TBMB) (FIG. 1a). The number of variable amino acids placed in between the cysteine residues were chosen to be 5 (library 5×5) or 3 (library 3×3 A) resulting in macrocycles with two rings of 22 and 28 atoms (FIG. 1b). An alanine residue was inserted at the N-terminus of the peptides to ensure proper cleavage of the signal peptide as well as a short peptide linker at the C-terminus. In the 3×3 library, the flanking exocyclic amino acids were optionally randomized (library 3×3 B) (FIG. 1a). Each library containing between 10$^8$ and 10$^{10}$ random peptides was separately subjected to 2-3 rounds of iterative selection and amplification using immobilized hPK. Sequencing of isolated peptides revealed strong consensus sequences in both peptide loops (FIG. 1c-e). Most peptides from the 5×5 library contained the sequence Xaa-Trp-Pro-Ala-Arg [SEQ ID No. 8] in the first loop and Leu-His-Gln-Asp-Leu [SEQ ID No. 9] in the second loop or similar sequences (FIG. 1c). Peptides isolated from the two 3×3 libraries had the consensus sequence Phe-Xaa-Xaa in the first loop and Arg-Val-Xaa in the second loop (FIGS. 1d and 1e). Several of the peptides were chemically synthesized with a free N-terminus and an amidated C-terminus and their inhibitory activity towards hPK was determined. From all the libraries, inhibitors with low nanomolar affinities could be isolated. In contrast to the previous phage selections with the 6×6 library, no affinity maturation was required to obtain inhibitors with single-digit K$_i$s.

The 3×3 and 5×5 peptide libraries are shown in tables 3 and 4.

Example 2: Determination of Specificity

Target Specificity Towards Paralogous Serine Proteases

The target specificity of the isolated bicyclic peptide inhibitors was assessed by determining the inhibition of trypsin-like human serine proteases of the class S1A which comprises 79 members (Yousef, et al, *Biochem Biophys Res Commun* 2003, 305 (1), 28-36). The panel of proteases included hfXIa which shares the highest sequence identity with hPK (69%) as well as the structurally less related but vital human serine proteases thrombin (36%), plasmin (34% sequence identity with hPK) and factor XIIa (35%). Similar as PK15, the two tested peptides isolated from the 5×5 library, 2A2 and 2A10, did not inhibit any of the paralogous proteases at the highest concentration tested (100 μM) with the exception of clone 2A10 which weakly inhibited human plasmin (K$_i$=27 μM). The smallest bicyclic peptides isolated from the 3×3 library did not inhibit thrombin, plasmin and factor XIIa, but inhibited hfXIa as effectively as hPK (e.g. clone 3B8: K$_i$ (hfXIa)=52 nM) (Table 1).

Inhibition of Plasma Kallikrein from Other Species

To assess if the inhibitors could potentially be tested in animal disease models, we determined their inhibitory activity towards rat and monkey (*Macaca mulatta*) plasma kallikrein (rPK and mPK). The two proteases have significant sequence identity with hPK, 81% (rPK) and 95% (mPK) respectively (Table 2). The proteases were transiently expressed as inactive precursors, having an N-terminal pro-TEV substrate sequence, in mammalian cells, and subsequently purified and activated. As a control we produced recombinant hPK, to compare the recombinant protein with blood plasma derived protein. While only a small fraction of the recombinant proteases could be activated, the comparison of active recombinant hPK and plasma derived hPK showed comparable catalytic properties (K$_M$) and gave the same inhibitory constants (K$_i$s) in inhibition assays.

The previously described hPK inhibitor PK15 having two peptide loops of 6 amino acids only inhibited the rPK at high bicyclic peptide concentrations (K$_i$=0.9 μM) (Table 1). In contrast, the monkey PK from *Macaca mulatta* (mPK) which shares 95% of the amino acids with hPK was inhibited by PK15 with a K$_i$ of 4 nM. The smaller bicyclic peptides derived from the 3×3 and 5×5 libraries were highly promiscuous towards monkey and rat PK, some inhibiting these orthologues with K$_i$s that are similar to those of hPK. The best activity toward rPK was measured for 2A2, the bicyclic peptide with 5-amino acid loops that showed no inhibition for all paralogous human proteases (K$_i$=7 nM).

The finding that 2A2 inhibits rPK with a low nanomolar K$_i$ allows now the testing of its therapeutic activity in murine disease models. A potent and selective bicyclic peptide inhibitor of PK has potential application in hereditary angioedema, an autosomal dominant disease caused by a deficiency of functional C1 inhibitor and in the inhibition of contact activation occurring for example in cardiopulmonary bypass surgery.

Figure 2:
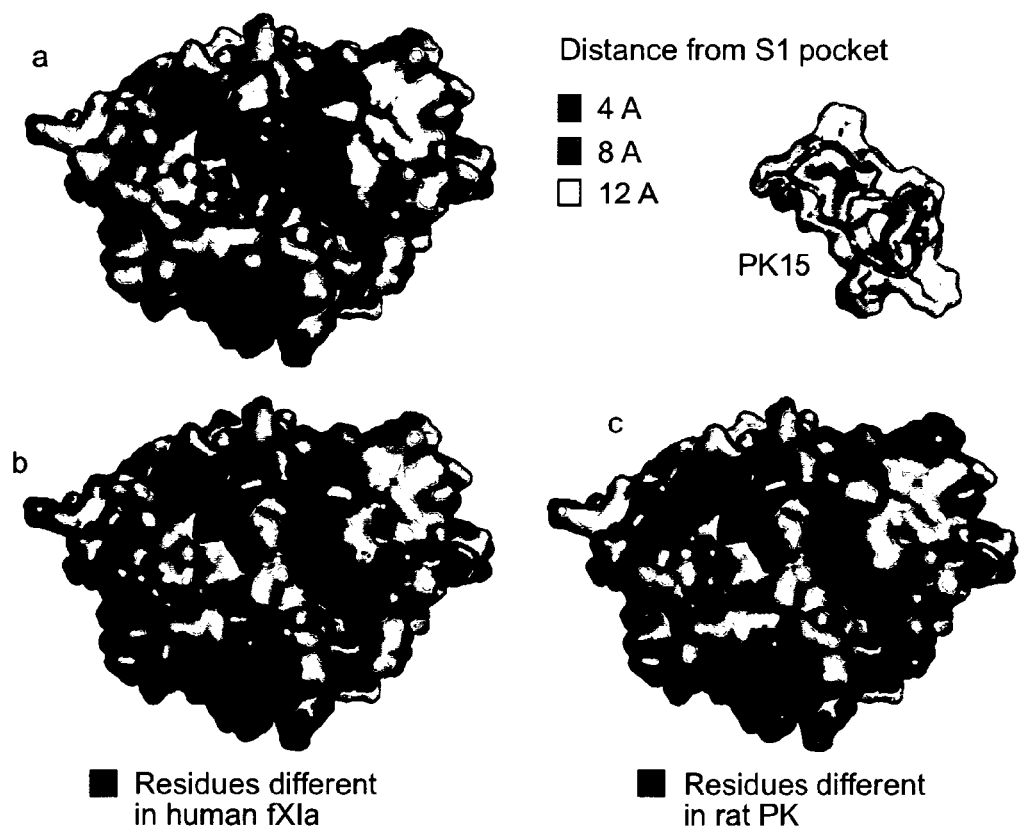
FIG. 2 Comparison of the surface amino acids of hPK and homologous serine proteases. (a) Structure of hPK (PDB entry 2ANW) with surface representation. Atoms of amino acids being exposed to the surface and closer than 4, 8 and 12 Å to benzamidine (in grey) bound to the S1 pocket are stained more darkly. (b) Structure of hPK. The side chains of amino acids that are different in hfXIa are highlighted. (c) Structure of hPK. The side chains of amino acids that are different in rPK are highlighted.

To understand the molecular basis of the selectivity of the differently sized bicyclic peptide inhibitors for hPK, hfXIa and rPK, we looked at the structural differences of these proteases around the active site (Table 2 and FIG. 2). Because bicyclic peptides isolated from all the different libraries contain arginine residues that are highly conserved within their consensus sequences, and it is likely that all the inhibitors bind with an arginine to the S1 specificity pocket of the trypsin-like serine proteases, we chose to analyze the surface region around the S1 binding site (Table 2 and FIG. 2a).

The 14 surface amino acids within a radius of 4 Å around the S1 binding pocket are identical in hfXIa and rPK, which does not suggest any difference in selectivity. However, at a greater distance from the S1 site, hfXIa differs to a greater extent from hPK and rPK: between 4 and 8 Å around the S1 site, hPK and hfXIa differ in 3 amino acids (hPK→hfXIa: E146L, R222Q, R224bK) while hPK and rPK are identical. And between 8 and 12 Å, the hPK and hfXIa differ in 6 amino acids (hPK→hfXIa: S97A, G99S, F143Y, S144R, K147R, G148D) while hPK and rPK differ in only 3 amino acids (hPK→rPK: F143Y, S144T, K147R). The amino acid changes between hPK and rPK are also more conserved (Table 2 and FIG. 2).

Without wishing to be bound by theory, it is suggested that a binding region of this size would fit well with the dimensions of a 5×5 bicyclic peptide and it is tempting to speculate that the 5×5 bicyclic peptides bind to a region of around 10×20 Å which is identical in the two orthologous proteases but differs in the two paralogous ones. Bicyclic peptides derived from the 3×3 libraries may interact only with amino acids close to the S1 site that are highly conserved in the three proteases and for this reason can't discriminate between them.

Example 4: Systematic Analysis of Plasma Stability

For a kallikrein-inhibiting bicycle, it is pertinent to obtain an adequate protease stability profile, such that it has a low protease-driven clearance in plasma or other relevant environments. In a rapid comparative plasma stability assay (methods section, method 1) that observed the progressive disappearance of parent peptide in rat plasma, it was found that the N-terminal alanine (which is present at the time of selections and was originally included in synthetic peptides of lead sequences) is rapidly removed across all bicycle sequences tested by both rat and human plasma. This degradation was avoided by synthesising a lead candidate lacking both N- and C-terminal alanines. To remove potential recognition points for amino- and carboxypeptidases, the free amino-terminus that now resides on Cys 1 of the lead candidate is capped with acetic anhydride during peptide synthesis, leading to a molecule that is N-terminally acetylated. In an equal measure, the C-terminal cysteine is synthesised as the amide so as to remove a potential recognition point for carboxypeptidases. Thus, bicyclic lead candidates have the following generic sequence: Ac-$C_1AA_1AA_2AA_nC_2AA_{n+1}AA_{n+2}AA_{n+3}C_3$(TMB)-NH2, where "Ac" refers to N-terminal acetylation, "—NH2" refers to C-terminal amidation, where "$C_1$, $C_2$, $C_3$" refers to the first, second and third cysteine in the sequence, where "$AA_1$" to "$AA_n$" refers to the position of the amino acid (whose nature "AA" is defined by the selections described above), and where "(TMB)" indicates that the peptide sequence has been cyclised with TBMB or any other suitable reactive scaffold.

Due to the high affinity of Ac-06-34-18(TMB)-NH2 to both human (Ki=0.17 nM) and rat kallikrein (IC50=1.7 nM), we chose this Bicycle for lead development. Using the same rapid plasma stability profiling assay described above, Ac-06-34-18(TMB)-NH2 had an observability window of about 2 days (methods section, method 1), which equates to a rat plasma halflife of ~2 hrs (as determined quantitatively by LC/MS, Table 6, method 3).

Figure 3:
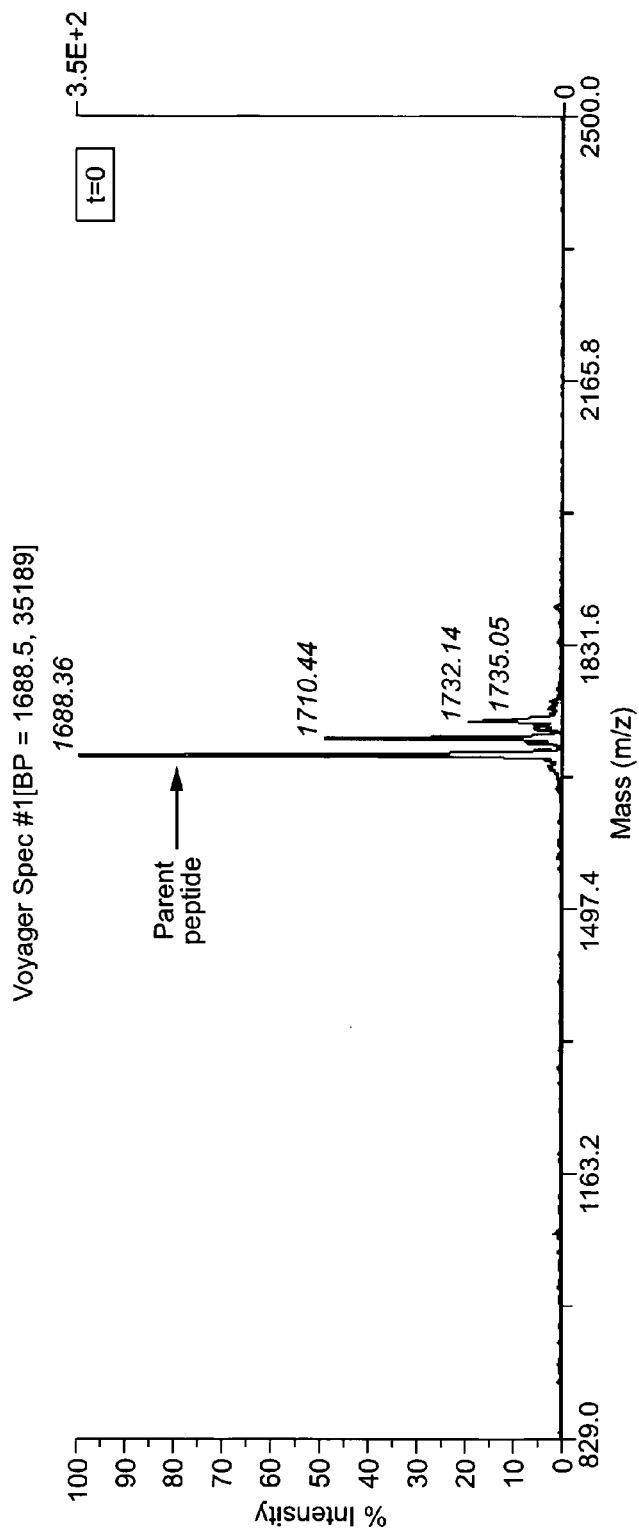
FIG. 3 Mass spec output showing the mass spectra of Ac-06-34-18(TMB)-NH2 after exposure to 35% rat plasma, at t0, 1 day, 2 days and 3 days (method 1). Mass accuracies vary somewhat due to interfering ions and low concentrations of fragments; however identification of discrete proteolytic fragments is possible.
Figure 3:
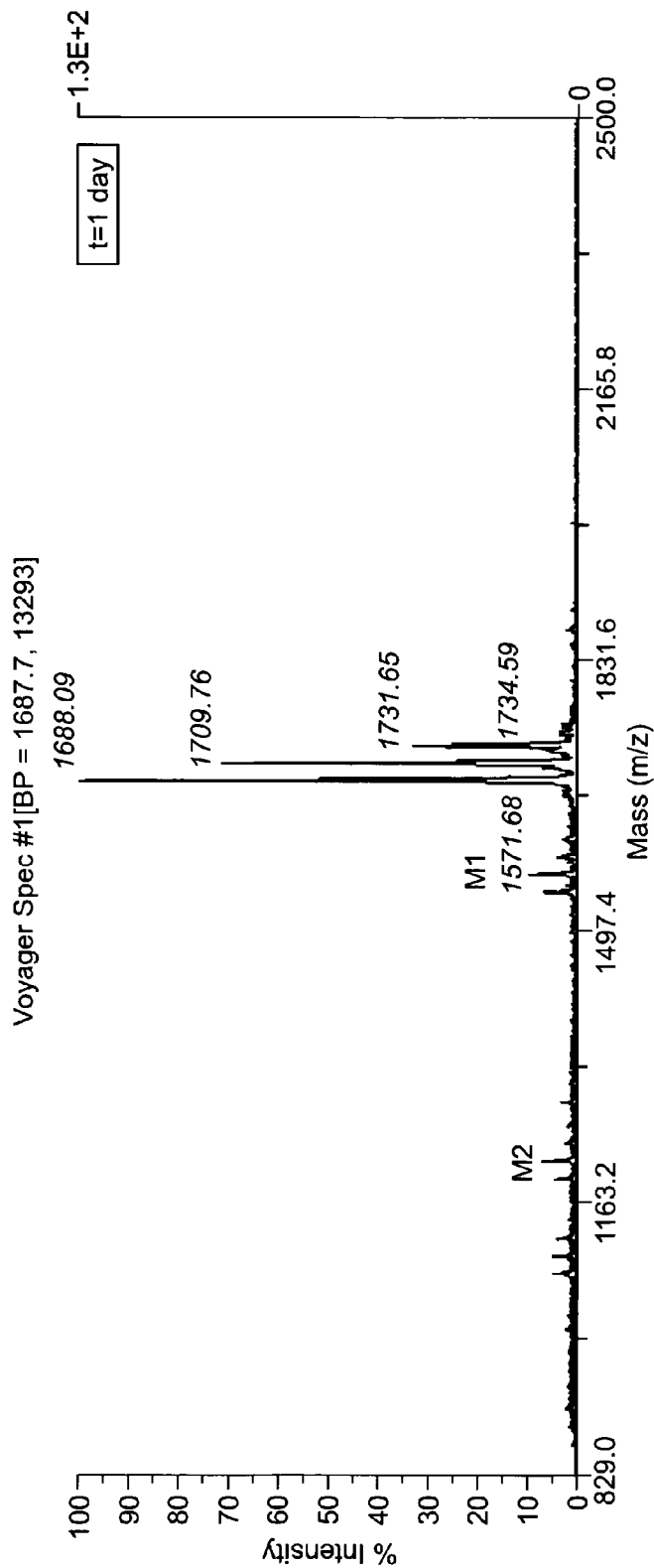
Figure 3:
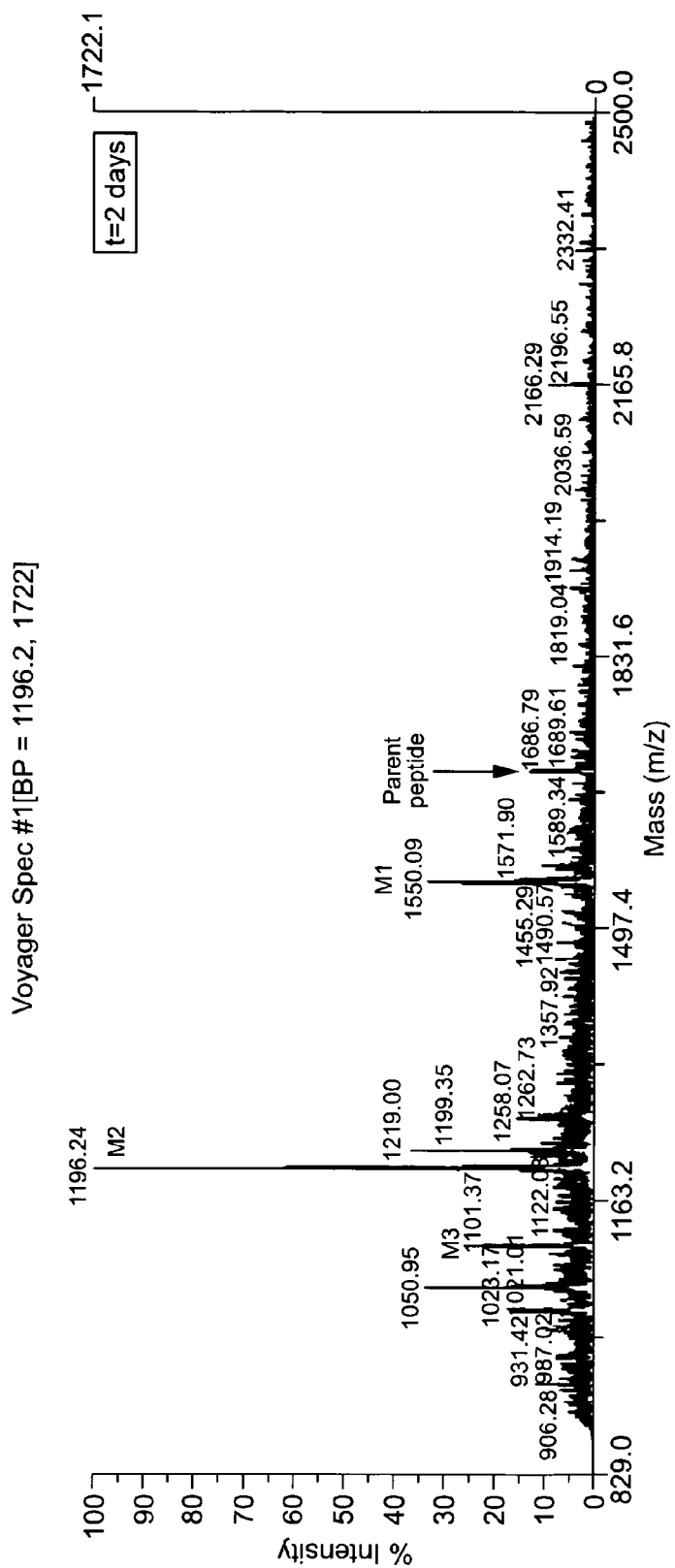
Figure 3:
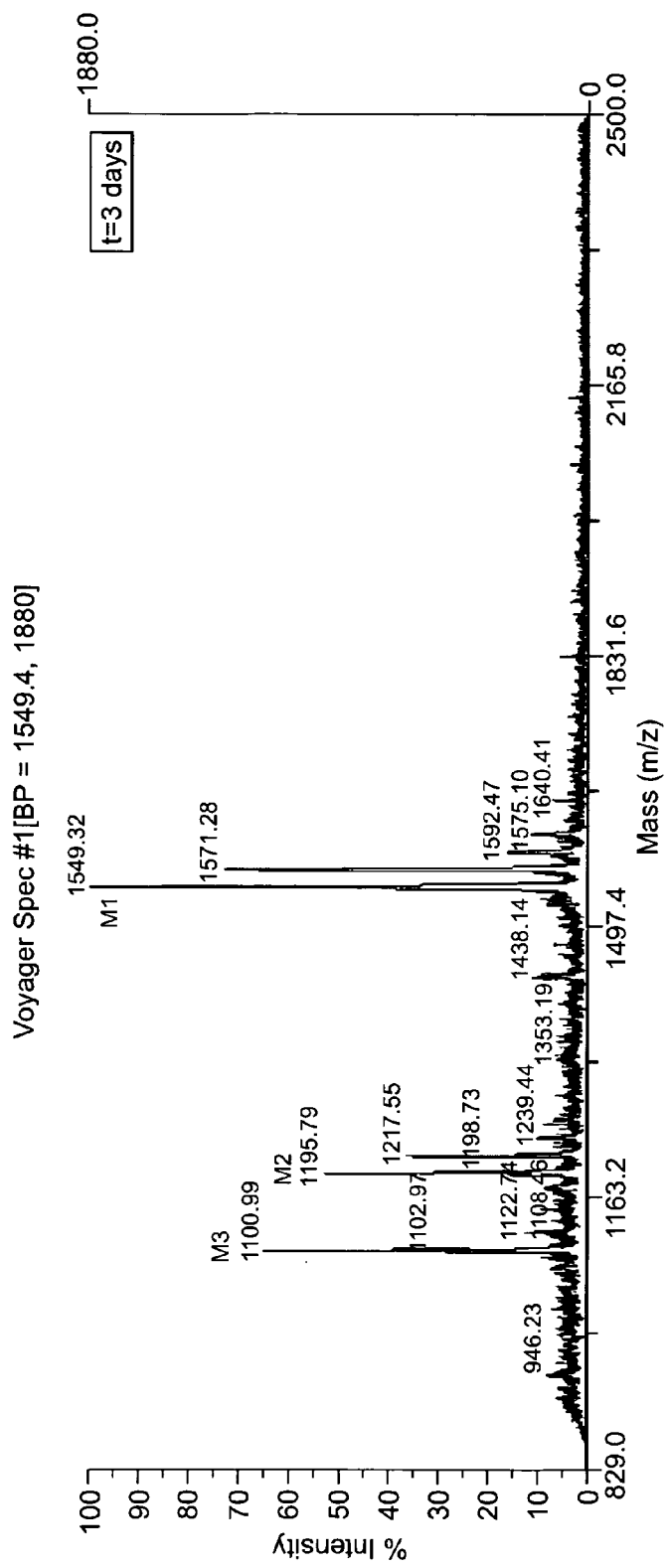
Figure 4:
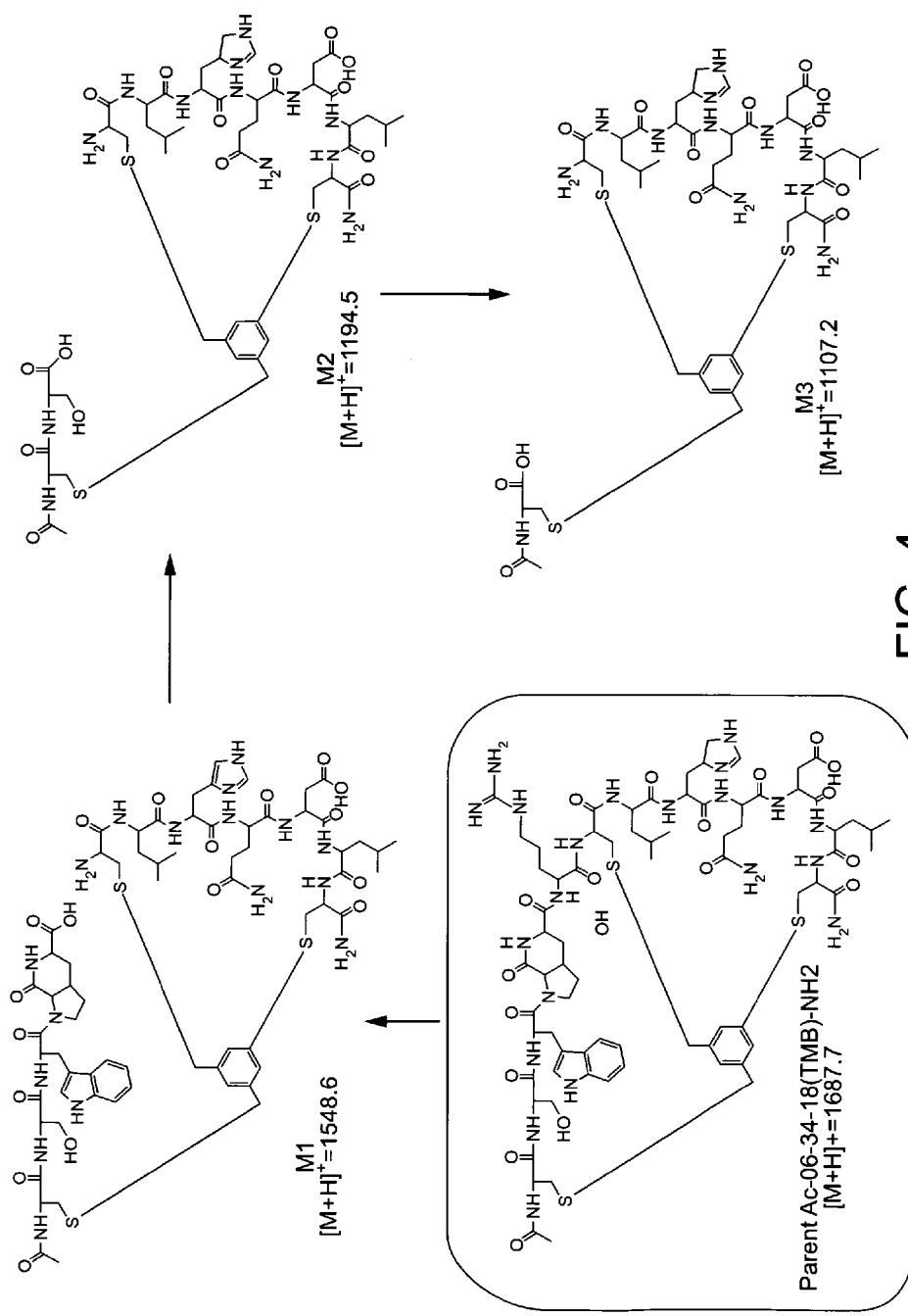
FIG. 4 Chemical structures of metabolites M1, M2, M3 of Ac-06-34-18(TMB)-NH2 identified after exposure to rat plasma.

In an effort to identify the proteolytic recognition site(s) in Ac-06-34-18(TMB)-NH2, the peptide was sampled in 35% rat plasma over time (method 1), and each sample was analysed for the progressive appearance of peptide fragments using MALDI-TOF mass spectrometry. The parent mass of Ac-06-34-18(TMB)-NH2 is 1687 Da. Over time (FIG. 3), fragments appear of the masses 1548.6 (M1), 1194.5 (M2), and 1107.2 (M3). From the sequence of Ac-06-34-18(TMB)-NH2 (Ac-$C_1S_1W_2P_3A_4R_5C_2L_6H_7Q_8D_9L_{10}C_3$—NH2) [SEQ ID No. 10], it can be calculated that the peak of M1 corresponds to Ac-06-34-18(TMB)-NH2 lacking Arg5 (-R5). This appears to be the initial proteolytic event, which is followed by removal of the 4-amino acid segment WPAR [SEQ ID No. 11] in Ac-06-34-18(TMB)-NH2 (M2, -WPAR [SEQ ID No. 11]), and finally the entire first loop of Ac-06-34-18(TMB)-NH2 is excised (M3, -SWPAR [SEQ ID No. 12]) (FIG. 4). From this data, it is evident that Arg5 of Ac-06-34-18 (TMB)-NH2 is the main rat plasma protease recognition site that is responsible the degradation of the Bicycle.

Figure 5A:
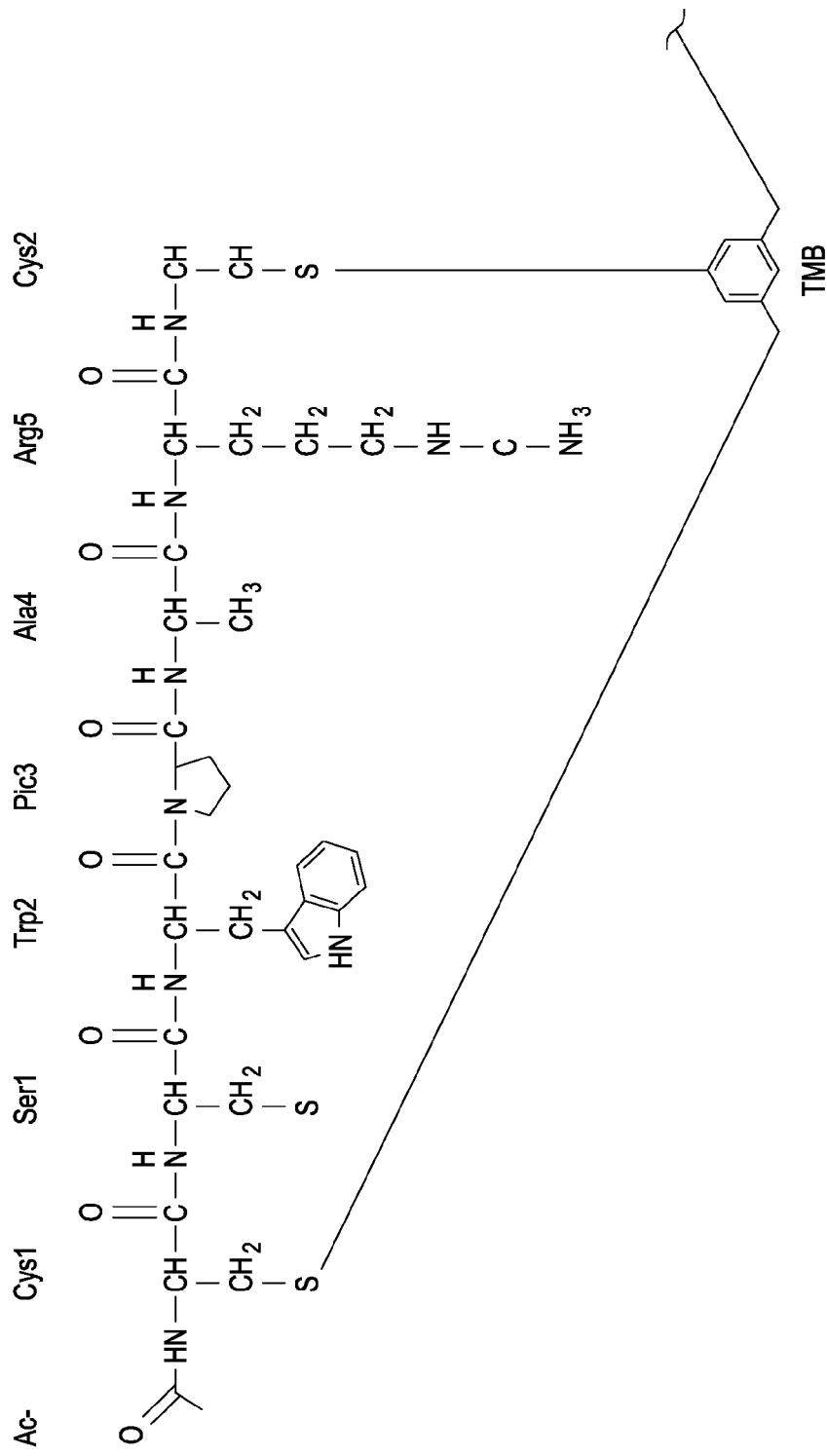
FIG. 5 Chemical structure of the Ac-06-34-18(TMB)-NH2 lead
Figure 5B:
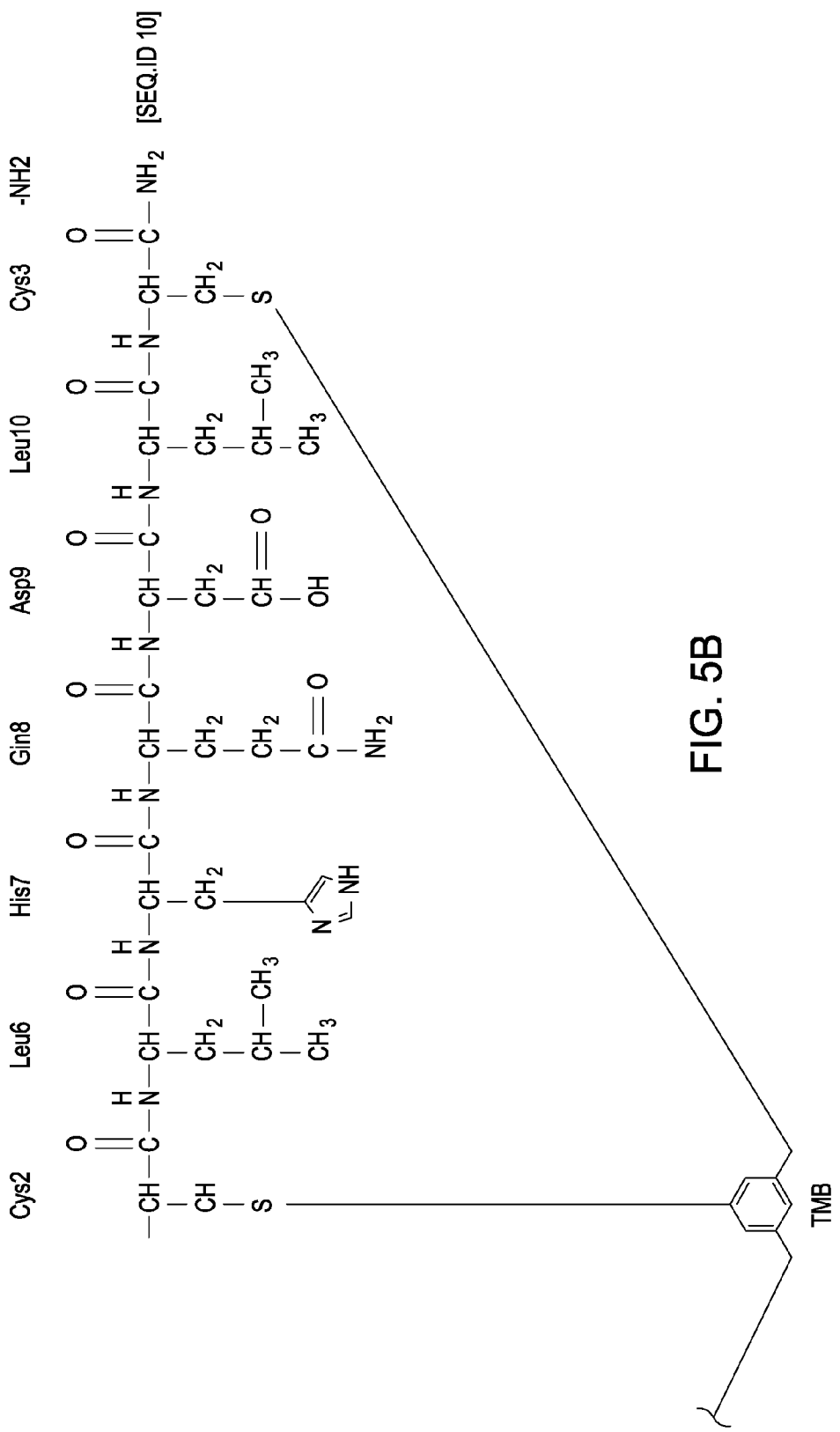

Alanine Substitutions and Scrambling of First Loop:

Having identified Arg5 in constituting the recognition site for rat plasma proteases, a campaign of chemical synthesis of Ac-06-34-18(TMB)-NH2 derivatives was undertaken with the aim of identifying candidates with higher plasma proteolytic stability. Crucially, such modifications should not affect the potency against human or rat kallikrein. An initial exploration regarding the role of the WPAR sequence/ pharmacophore (FIG. 5) was performed by replacing $W_2P_3$ with $A_2A_3$ or $A_2Q_3$ and by scrambling parts or the entire first loop of the bicycle. Table 6 below shows the sequences and the respective affinities against Kallikrein.

Figure 6:
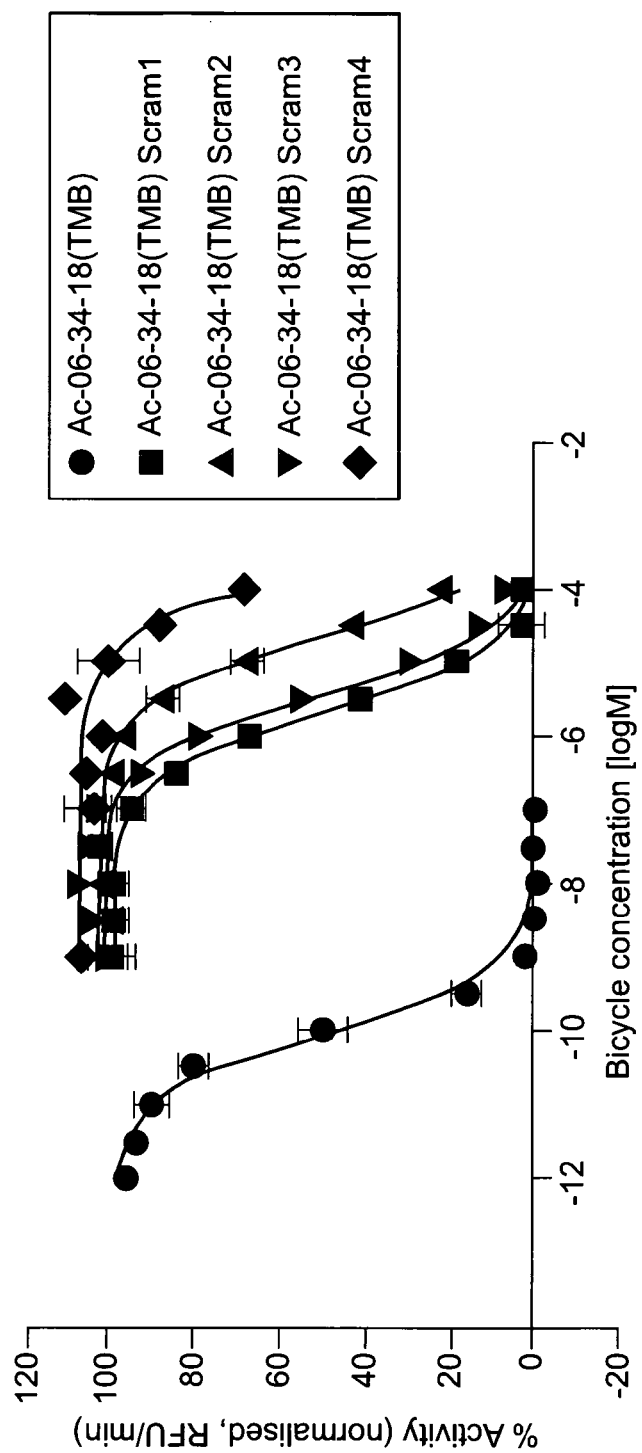
FIG. 6 Enzyme inhibition assay of kallikrein by the Ac-06-34-18(TMB)-NH2 lead and its $1^{st}$ loop scrambled derivatives. A dramatic reduction in affinity is observed, underlining the importance of the integrity of the WPAR pharmacophore.

From these data it is clear that concomitant removal of $W_2P_3$ dramatically reduces binding to kallikrein by a factor of ~100000, effectively rendering the molecule pharmacologically inert. The importance of the correct sequence of the amino acids is underlined by the four scrambled peptides (Scram2-4), as all of them display a substantial reduction in affinity towards kallikrein (FIG. 6). Curiously, all peptides have a roughly identical rat plasma stability profile (between 1 to 2 days, method 1), indicating that plasma protease recognition relies on the presence of the arginine (Table 6), and not on its position within the sequence.

Next, five derivatives of Ac-06-34-18(TMB)-NH2 were generated where $W_2$, $P_3$, $A_4$, $R_5$, and $C_2$ were replaced with their respective D-enantiomeric counterparts (Table 7).

From the data it is clear that D-amino acid replacement of $A_4$, $R_5$, and $C_2$ increase peptide stability towards plasma proteases. As Arg5 excision by rat plasma proteases appears to be the first event in peptide degradation, the initial hydrolysis of peptide bonds will occur on the N- and/or C-terminal side of Arg5. It is plausible that replacing the amino acids to either side of Arg5 with their D-enantiomers blocks adjacent peptide bond hydrolysis through steric hindrance. Indeed, this is an effect that has been observed previously (Tugyi et al (2005) PNAS, 102(2), 413-418).

The detrimental effect of D-amino acid substitution on affinities to kallikrein is striking in all cases; losses in potencies range from 300- (D-Arg5) to 45000-fold (D-Trp2). This underlines the importance of the correct three-dimensional display of these sidechains to the kallikrein bicycle binding pocket. Equally striking is the effect of D-Ala4: here, changing the orientation of a single methyl group (being the Ala side chain) reduces the affinity 7000-fold.

N-Methylations:

Next, residues in the first loop were systematically replaced with their N-methyl counterparts. N-methylation serves as a straightforward protection of the peptide bond itself; however, due to the absence of the amide hydrogen, addition of steric bulk (the methyl group) and changes in preferred torsional angles, losses in potencies are expected.

Table 8 summarises the data.

N-methylation of amino acids in loop 1 displays an altogether less drastic detrimental effect on potency. In particular, N-methylation of Arg5 still yields a single digit nanomolar binder (20-fold reduction in affinity compared to wildtype peptide), and its rat plasma stability exceeds the assay time (fragmentation of the peptide in the MS was not observable), making this an attractive improved lead candidate. As with the D-amino acid substitutions, N-methylation of residues adjacent to Arg5 imparts enhanced stability to the peptide, presumably through steric interference affecting protease-catalysed hydrolysis of peptide bonds N and/or C-terminal to Arg5. Of note, Ser1 can be N-methylated without a significant loss in potency, indicating that the integrity of the peptide backbone in this position is not essential for binding.

Figure 7:
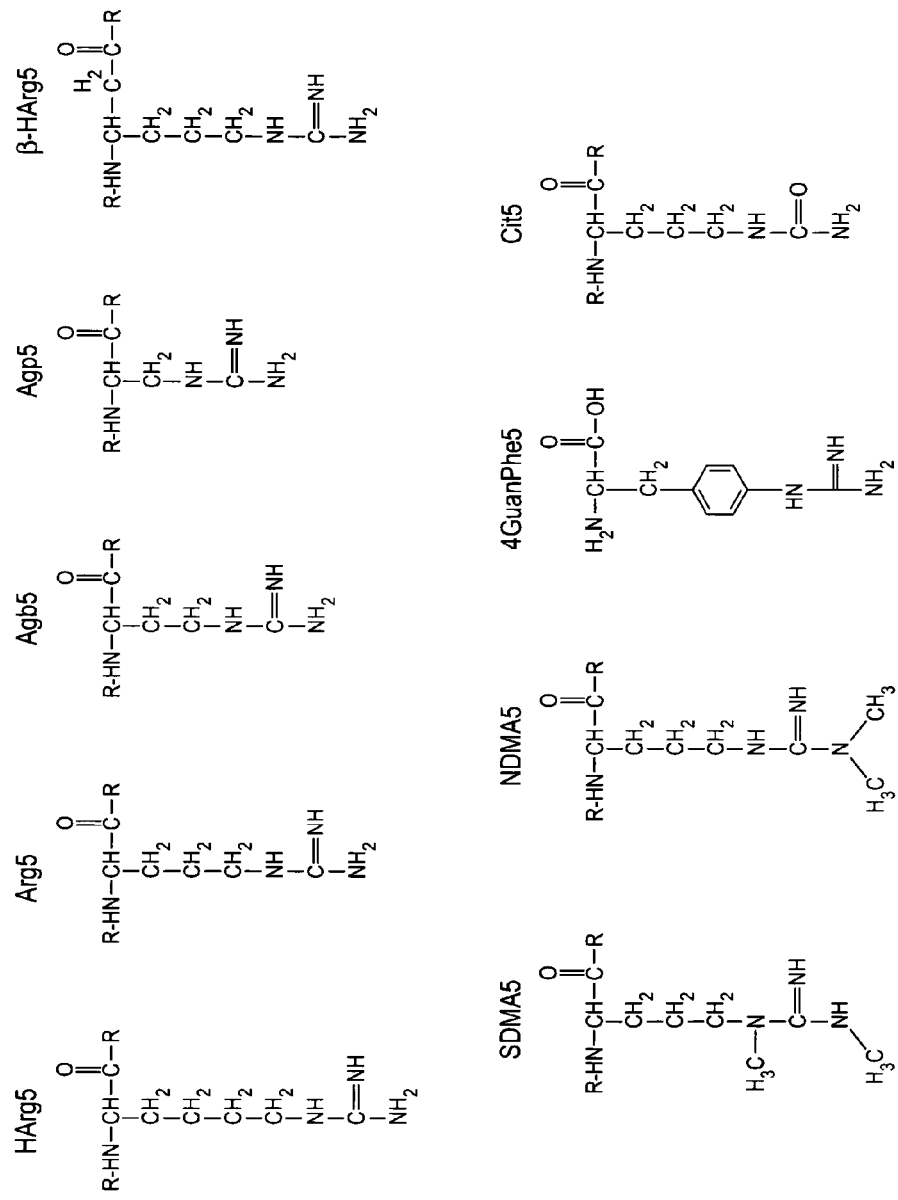
FIG. 7 Chemical structures of arginine and its analogues.

Arginine Substitutions:

Given the importance of Arg5 in recognition by rat plasma proteases, a set of arginine analogues were tested in the Ac-06-34-18(TMB)-NH2 lead. The chemical structures are shown in FIG. 7, and the potency versus stability data is shown in Table 9.

Strikingly, all arginine analogues increase the stability of the peptide beyond the assay window time, confirming the importance of the integrity of Arg5 in plasma protease recognition. Increasing (HomoArg) or decreasing the length of the side chain (Agb, Agp) both decrease affinity, however the HomoArg analogue still yields a very good binder (Ki=2.1 nM), with enhanced stability. Lengthening the amino acid backbone by one methylene group in Arg5 (a so-called beta-amino acid) while retaining the same side chain (β-homoArg5) also yields a binder with enhanced stability, however at the price of a more significant reduction in affinity (Ki=8.2 nM). Replacing the aliphatic part of the Arg side chain with a phenyl ring yields a resonance stabilised, bulkier and rigidified guanidyl-containing side chain (4GuanPhe). Of all the Arg analogues tested, 4GuanPhe had the greatest affinity (2-fold reduction compared to wildtype), at an enhanced plasma stability. Interestingly, the guanidylphenyl group is structurally close to the known small molecule kallikrein inhibitor benzamidine (Stürzebecher et al (1994), *Novel plasma kallikrein inhibitors of the benzamidine type*. Braz J Med Biol Res. 27(8):1929-34; Tang et al (2005), *Expression, crystallization, and three-dimensional structure of the catalytic domain of human plasma kallikrein*. J. Biol. Chem. 280: 41077-89). Furthermore, derivatised Phenylguanidines have been employed as selective inhibitors of another serine protease, uPA (Sperl et al, (4-*aminomethyl*)*phenylguanidine derivatives as nonpeptidic highly selective inhibitors of human urokinase* (2000) Proc Natl Acad Sci USA. 97(10):5113-8.). Thus, Ac-06-34-18(TMB)-NH2 containing 4GuanPhe5 can be viewed as a small molecule inhibitor, whose selectivity is imparted by the surrounding Bicyclic peptide. This can comprise a principle for other bicycle-based inhibitors, where a known small molecule inhibitor of low selectivity is "grafted" onto a Bicycle in the correct position, leading to a molecule of superior potency and selectivity.

Modification of the Arg guanidyl-group itself, either by methylation (SDMA, NDMA), removal of the positive charge (Cit, where the guanidyl group is replaced by the isosteric but uncharged urea group) or deletion of the Arg altogether (A Arg) has strongly detrimental effects on kallikrein binding potency. Thus, the integrity and presence of the guanidyl group is crucial, while the nature of the sidechain connecting to the guanidyl group or backbone at Arg5 is not. Of note, Arg5 may also be replaced by lysine, however again at reduced affinities (see WPAK [SEQ ID No. 13] peptide).

In summary, data this far indicates that Ac-06-34-18 (TMB)-NH2 employing either HomoArg, NMeArg or 4GuanPhe as arginine replacements could constitute plasma stability enhanced candidates with high affinities.

TABLES

TABLE 1

Target specificity of bicyclic peptides with different loop lengths. Indicated are $K_i$ values for hPK and different paralogous and orthologous proteases. $K_i$ values are means of at least two measurements.

| Bicyclic peptide | Number of amino acids in loops | $K_i$ (nM) | | | | | | |
|---|---|---|---|---|---|---|---|---|
| | | | Orthologous proteases | | Paralogous proteases | | | |
| | | Human plasma kallikrein (hPK) | Monkey plasma kallikrein (monkeyPK) | Rat plasma kallikrein (rPK) | Human factor XIa (hfXIa) | Human thrombin | Human plasmin | Human factor XIIa (hfXIIa) |
| PK15 | 6 × 6 | 2.9 +/− 0.9 | 2.9 +/− 0.6 | 2'089 +/− 860 | >50'000 | >50'000 | >50'000 | >50'000 |
| PK117 | 3 × 3 | 5.2 +/− 1.8 | 2.8 +/− 1.7 | 27.2 +/− 14.0 | 40.4 +/− 11.9 | >50'000 | >50'000 | >50'000 |
| PK123 | | 5.2 +/− 1.9 | 4.4 +/− 1.1 | 14.0 +/− 8.2 | 39.7 +/− 11.9 | >50'000 | >50'000 | >50'000 |
| PK132 | | 37.1 +/− 8.1 | 12.2 +/− 7.4 | 59.7 +/− 29.4 | 526 +/− 46 | >50'000 | >50'000 | >50'000 |
| PK100 | 5 × 5 | 0.4 +/− 0.1 | 1.1 +/− 0.5 | 24.0 +/− 4.0 | 2'502 +/− 231 | >50'000 | >50'000 | >50'000 |
| PK101 | | 0.3 +/− 0.0 | 0.4 +/− 0.1 | 11.0 +/− 2.0 | 19'739 +/− 1912 | >50'000 | >50'000 | >50'000 |
| PK104 | | 0.9 +/− 0.1 | 2.5 +/− 0.8 | 38 +/− 7.9 | 12'907 +/− 1490 | >50'000 | >50'000 | >50'000 |
| PK106 | | 2.9 +/− 1.2 | 2.0 +/− 1.1 | 6.6 +/− 2.3 | >50'000 | >50'000 | >50'000 | >50'000 |
| PK112 | | 12.2 +/− 4.8 | 9.4 +/− 1.5 | 37.5 +/− 14.2 | >50'000 | >50'000 | 24'137 +/− 1796 | >50'000 |
| PK114 | | 4.3 +/− 0.2 | 2.0 +/− 0.6 | 16.6 +/− 0.9 | >50'000 | >50'000 | >50'000 | >50'000 |
| PK116 | | 5.3 +/− 2.6 | 6.0 +/− 2.8 | 27.7 +/− 11.8 | >50'000 | >50'000 | >50'000 | >50'000 |

TABLE 2

Sequence homologies around the active site of paralogous and orthologous serine proteases of hPK.

| | | | Sequence identity with human plasma kallikrein (hPK) | | | | | |
|---|---|---|---|---|---|---|---|---|
| | | | Orthologous proteases | | Paralogous proteases | | | |
| Compared region | | Number of amino acids | Monkey plasma kallikrein (mPK) | Rat plasma kallikrein (rPK) | Human factor XIa (hfXIa) | Human thrombin | Human plasmin | Human factor XIIa |
| All amino acids | | | 95% | 81% | 69% | 36% | 34% | 35% |
| Surface amino acids within a specific distance of the active site* | 4 Å | 14 | 100% | 100% | 100% | 71% | 86% | 79% |
| | 8 Å | 19 | 100% | 100% | 83% | 79% | 74% | 63% |
| | 12 Å | 41 | 100% | 93% | 84% | 61% | 54% | 56% |

*Based on the crystal structure of hPK (PDB entry 2ANW) wherein the bound benzamidine ligand in the S1 pocket was chosen as center.

TABLE 3

3 × 3 peptides

| Peptide | Sequence | Seq ID No. | | Kallikrein Av Ki (nM) | Thrombin Ic50 |
|---|---|---|---|---|---|
| 3B8 | ACFKHCRVACA | SEQ ID NO. 14 | A C F K H C R V A C A | 0.95 | >10000 |
| 3A3 | ACFPKCRVACA | SEQ ID NO. 15 | A C F P K C R V A C A | 43.1 | |
| 3B9 | ACFDPCRVICA | SEQ ID NO. 16 | A C F D P C R V I C A | 90.8 | |
| 3B2 | ACFKNCRVNCA | SEQ ID NO. 17 | A C F K N C R V N C A | 9 | |
| 06-64 | ACFNKCRVNCA | SEQ ID NO. 18 | A C F N K C R V N C A | 4.8 | |
| 06-94 | ACFKQCRVNCA | SEQ ID NO. 19 | A C F K Q C R V N C A | 0.7 | >10000 |
| 06-71 | ACFYKCRVNCA | SEQ ID NO. 20 | A C F Y K C R V N C A | 15.2 | |
| 3B3 | ACFKACRVNCA | SEQ ID NO. 21 | A C F K A C R V N C A | 0.59 | >10000 |

TABLE 4

5 × 5 peptides

| | Sequence | SEQ ID No. | | Kallikrein Av Ki (nM) | Thrombin Ic50 | Factor XIIa |
|---|---|---|---|---|---|---|
| 06-01 | ACAWPARCLTVDLCA | SEQ ID NO. 22 | A C A W P A R C L T V D L C A | <0.1* | >10000 | >10000 |
| 06-34 | ACRWPARCVHQDLCA | SEQ ID NO. 23 | A C R W P A R C V H Q D L C A | <0.3* | >10000 | >10000 |
| 06-57 | ACSWPARCNHQDLCA | SEQ ID NO. 24 | A C S W P A R C N H Q D L C A | 0.4 | >10000 | >10000 |
| 06-59 | ACRWPARCLTTSLCA | SEQ ID NO. 25 | A C R W P A R C L T T S L C A | 0.5 | >10000 | >10000 |
| 06-54 (2A2) T | ACRWPARCTHQNYCA | SEQ ID NO. 26 | A C R W P A R C T H Q N Y C A | 0.49 | >10000 | >10000 |
| 06-09 | ACTWPARCTHQNWCA | SEQ ID NO. 27 | A C T W P A R C T H Q N W C A | 1.2 | >10000 | >10000 |
| 06-143 | ACFPSHDCDGRRMCA | SEQ ID NO. 28 | A C F P S H D C D G R R M C A | 1.27 | >10000 | >10000 |
| 06-56 | ACGGPQNCRTWTTCA | SEQ ID NO. 29 | A C G G P Q N C R T W T T C A | 2.1 | >10000 | >10000 |
| 06-157 | ACNWPYRCLHTDLCA | SEQ ID NO. 30 | A C N W P Y R C L H T D L C A | 3.3 | >10000 | >10000 |
| 06-61 | ACSWPYRCLHQDYCA | SEQ ID NO. 31 | A C S W P Y R C L H Q D Y C A | 5.8 | >10000 | >10000 |
| 06-64 T | ACGVPYRCTHQEMCA | SEQ ID NO. 32 | A C G V P Y R C T H Q E M C A | 6.9 | >10000 | >10000 |

TABLE 4-continued 5 x 5 peptides

| | Sequence | SEQ ID No. | | Kallikrein Av Ki (nM) | Thrombin Ic50 | Factor XIIa |
|---|---|---|---|---|---|---|
| 06-A2* | ACTWPARCTMQNWCA | SEQ ID NO. 33 | A C T W P A R C T M Q N W C A | 181 | | >10000 |
| 06-63 T | ACADPWACLFRRPCA | SEQ ID NO. 34 | A C A D P W A C L F R R P C A | 1277 | >10000 | >10000 |
| 1E6 | ACAWPARCLTTSLCGS | SEQ ID NO. 35 | A C A W P A R C L T T S L C G | 0.16 | >10000 | >10000 |
| 2A10 | ACTYPYKCLHQNLCA | SEQ ID NO. 36 | A C T Y P Y K C L H Q N L C A | 4.98 | | |
| 1B1 | ACAWPAKCLTRELCA | SEQ ID NO. 37 | A C A W P A K C L T R E L C A | 8.1 | | |
| 1F7 | ACGGYNNCRAFSYCA | SEQ ID NO. 38 | A C G G Y N N C R A F S Y C A | 2.2 | | |

TABLE 5

| Supplier | Short name | Full chemical name |
|---|---|---|
| AGTC | D-Asp | Fmoc-D-Asp(tBu)-OH |
| Anaspec | NDM-Arg | Fmoc-Nωdimethyl-L-arginine |
| Anaspec | NMe-Ser | Fmoc-Nα-methyl-O-t-butyl-L-serine |
| Anaspec | NMe-Trp | Fmoc-Nα-methyl-L-tryptophan |
| Anaspec | NorHar | Fmoc-L-1;2;3;4-tetrahydro-norharman-3-carboxylic acid |
| Anaspec | 4PhenylPro | Fmoc-(2S;4S)-4-phenyl-pyrrolidine-2-carboxylic acid |
| Iris Biotech | Agb | Fmoc-L-Agb(Boc)2-OH |
| Iris Biotech | Agp | Fmoc-L-Agp(Boc)2-OH |
| Iris Biotech | β-Ala | Fmoc-beta-Ala-OH |
| Iris Biotech | Cit | Fmoc-Cit-OH |
| Iris Biotech | D-Cys | Fmoc-D-Cys-OH |
| Iris Biotech | β-HArg | Fmoc-L-beta-HArg(Pbf)-OH |
| Iris Biotech | NMe-Arg | Fmoc-L-MeArg(Mtr)-OH |
| Iris Biotech | 3Pal | Fmoc-L-3Pal-OH |
| Iris Biotech | 4Pal | Fmoc-L-4Pal-OH |
| Iris Biotech | Pen | Fmoc-Pen(Trt)-OH |
| Iris Biotech | D-Pro | Fmoc-D-Pro-OH |
| Iris Biotech | Tic | Fmoc-L-Tic-OH |
| Iris Biotech | D-Trp | Fmoc-D-Trp-OH |
| Merck Novabiochem | Aib | Fmoc-Aib-OH |
| Merck Novabiochem | D-Ala | Fmoc-D-Ala-OH |
| Merck Novabiochem | D-Arg | Fmoc-D-Arg(Pbf)-OH |
| Merck Novabiochem | 4GuanPhe | Fmoc-Phe(bis-Boc-4-guanidino)-OH |
| Merck Novabiochem | D-Gln | Fmoc-D-Gln(Trt)-OH |
| Merck Novabiochem | D-His | Fmoc-D-His(Trt)-OH |
| Merck Novabiochem | Hyp | Fmoc-Hyp(tBu)-OH |
| Merck Novabiochem | D-Leu | Fmoc-D-Leu-OH |
| Merck Novabiochem | NMe-Ala | Fmoc-L-MeAla-OH |
| Merck Novabiochem | NMe-Cys | Fmoc-N-Me-Cys(Trt)-OH |
| Merck Novabiochem | SDMA | Fmoc-SDMA(Boc)2-ONa |
| Merck Novabiochem | HArg | Fmoc-L-HArg(Boc)2-OH |
| Peptech Corporation | 4,4-BPAl | Fmoc-L-4,4'-Biphenylalanine |
| Peptech Corporation | 3,3-DPA | Fmoc-L-3,3-Diphenylalanine |
| Peptech Corporation | Dpg | Fmoc-Dipropylglycine |
| Peptech Corporation | 1NAl | Fmoc-L-1-Naphthylalanine |
| Peptech Corporation | 2NAl | Fmoc-L-2-Naphthylalanine |
| Peptech Corporation | Pip | Fmoc-L-Pipecolic acid |
| Polypeptide Group | Aba | Fmoc-L-2-aminobutyric acid |
| Polypeptide Group | Aze | Fmoc-L-azetidine-2-carboxylic acid |
| Polypeptide Group | 4BenzylPro | (2S,4R)-Fmoc-4-benzyl-pyrrolidine-2-carboxylic acid |
| Polypeptide Group | Cha | Fmoc-beta-cyclohexyl-L-alanine |
| Polypeptide Group | 4FluoPro | (2S,4R)-Fmoc-4-fluoro-pyrrolidine-2-carboxylic acid |
| Polypeptide Group | Ind | Fmoc-L-Indoline-2-carboxylic acid |

TABLE 6

| Peptide | Sequence | Seq ID No. | Ki (nM) (human kallikrein) | Observable in rat plasma, for days |
|---|---|---|---|---|
| Ac-(06-34-18) wild-type | Ac-CSWPARCLHQDLC | SEQ ID NO. 10 | 0.17 | 2 |

TABLE 6-continued

| Peptide | Sequence | Seq ID No. | Ki (nM) (human kallikrein) | Observable in rat plasma, for days |
|---|---|---|---|---|
| Ac-(06-34-18) A2A3 | Ac-CSAAARCLHQDLC | SEQ ID NO. 39 | 18545 | 1 |
| Ac-(06-34-18) A2Q3 | Ac-CSAQARCLHQDLC | SEQ ID NO. 40 | 15840 | 1 |
| Ac-(06-34-18) Scram1 | Ac-CPSAWRCLHQDLC | SEQ ID NO. 41 | 1091 | 2 |
| Ac-(06-34-18) Scram2 | Ac-CWASPRCLHQDLC | SEQ ID NO. 42 | 11355 | 2 |
| Ac-(06-34-18) Scram3 | Ac-CAPWSRCLHQDLC | SEQ ID NO. 43 | 1892 | 1 |
| Ac-(06-34-18) Scram4 | Ac-CWARSPCLHQDLC | SEQ ID NO. 44 | 67500 | 1 |

TABLE 7

Comparative effects of D-amino acid substitution on potency and rat plasma stability.

| Peptide | Ki (nM) (human kallikrein) | Observable in rat plasma, for days |
|---|---|---|
| Ac-(06-34-18) wildtype | 0.17 | 2 |
| Ac-(06-34-18) D-Trp2 | 7558 | 2 |
| Ac-(06-34-18) D-Pro3 | 680 | 3 |
| Ac-(06-34-18) D-Ala4 | 1203 | >10 |
| Ac-(06-34-18) D-Arg5 | 52 | >10 |
| Ac-(06-34-18) D-Cys2 | 234 | >10 |

TABLE 8

Comparative effects of N-methylation of loop 1 residues and Cys2 on potency and rat plasma stability.

| Peptide | Ki (nM) (human kallikrein) | Observable in rat plasma, for days |
|---|---|---|
| Ac-(06-34-18) wildtype | 0.17 | 2 |
| Ac-(06-34-18) NMeSer1 | 0.5 | 3 |
| Ac-(06-34-18) NMeSer1, NMeAla4 | 444 | >10 |
| Ac-(06-34-18) NMeTrp2 | 228 | 5 |
| Ac-(06-34-18) NMeAla4 | 343 | >10 |

TABLE 8-continued

Comparative effects of N-methylation of loop 1 residues and Cys2 on potency and rat plasma stability.

| Peptide | Ki (nM) (human kallikrein) | Observable in rat plasma, for days |
|---|---|---|
| Ac-(06-34-18) NMeArg5 | 3.5 | >10 |
| Ac-(06-34-18) NMeCys2 | 418 | 10 |

TABLE 9

Comparative effects of arginine analogues in Ac-06-34-18(TMB)-NH2 on potency and stability. Note that the Δ Arg modification did not display any inhibition up to 100 μM peptide.

| Peptide | Ki (nM) (human kallikrein) | Observable in rat plasma, for days |
|---|---|---|
| Ac-(06-34-18) wildtype | 0.17 | 2 |
| Ac-(06-34-18) HomoArg5 | 2.1 | >10 |
| Ac-(06-34-18) Agb5 | 83 | >10 |
| Ac-(06-34-18) Agp5 | 1770 | >10 |
| Ac-(06-34-18) βhomoArg5 | 8.2 | >10 |
| Ac-(06-34-18) 4GuanPhe5 | 0.3 | >10 |
| Ac-(06-34-18) SDMA5 | 1415 | >10 |
| Ac-(06-34-18) NDMA5 | 510 | >10 |
| Ac-(06-34-18) CitS | 7860 | >10 |
| Ac-(06-34-18) Δ Arg5 | >100000 | >10 |

The invention claimed is:

1. A polypeptide ligand comprising a polypeptide comprising at least three reactive groups, separated by at least two loop sequences and comprising the sequence $AC(X)_4JC(X)_5CG$ [SEQ ID No: 1], wherein X is a random natural amino acid, A is Alanine, C is Cysteine, G is Glycine, and J is N-methyl Arginine, Homo-Arginine, or Guanidylphenylalanine; and a molecular scaffold which forms covalent bonds with the reactive groups of the polypeptide such that at least two polypeptide loops are formed on the molecular scaffold and the polypeptide ligand is resistant to protease degradation.

2. The polypeptide ligand according to claim 1, wherein the polypeptide ligand comprises only two loops.

3. The polypeptide ligand according to claim 1, wherein the polypeptide ligand comprises three loops.

4. The polypeptide ligand according to claim 1, which is specific for a protease.

5. The polypeptide ligand according to claim 4, wherein the protease is plasma kallikrein.

* * * * *

SEQUENCE LISTING

<160> NUMBER OF SEQ ID NOS: 65

<210> SEQ ID NO 1
<211> LENGTH: 17
<212> TYPE: PRT
<213> ORGANISM: Artificial sequence
<220> FEATURE:
<223> OTHER INFORMATION: Synthetic peptide
<220> FEATURE:
<221> NAME/KEY: VARIANT
<222> LOCATION: (3)..(8)
<223> OTHER INFORMATION: Xaa at positions 3-8 may be any random natural
      amino acid and up to three of them may be absent; represents a
      range of between 3 and 6 amino acids.
<220> FEATURE:
<221> NAME/KEY: VARIANT
<222> LOCATION: (10)..(15)
<223> OTHER INFORMATION: Xaa at positions 10-15 may be any random
      natural amino acid and up to three of them may be absent;
      represents a range of between 3 and 6 amino acids.

-continued

<400> SEQUENCE: 1

Ala Cys Xaa Xaa Xaa Xaa Xaa Xaa Cys Xaa Xaa Xaa Xaa Xaa Xaa Cys
1               5                   10                  15

Gly

<210> SEQ ID NO 2
<211> LENGTH: 4
<212> TYPE: PRT
<213> ORGANISM: Artificial sequence
<220> FEATURE:
<223> OTHER INFORMATION: Synthetic sequence: Linker

<400> SEQUENCE: 2

Gly Gly Ser Gly
1

<210> SEQ ID NO 3
<211> LENGTH: 32
<212> TYPE: DNA
<213> ORGANISM: Artificial sequence
<220> FEATURE:
<223> OTHER INFORMATION: Synthetic sequence: Primer prepcr

<400> SEQUENCE: 3
ggcggttctg gcgctgaaac tgttgaaagt ag                                32

<210> SEQ ID NO 4
<211> LENGTH: 41
<212> TYPE: DNA
<213> ORGANISM: Artificial sequence
<220> FEATURE:
<223> OTHER INFORMATION: Synthetic sequence: Primer sfi2fo

<400> SEQUENCE: 4
gaagccatgg cccccgaggc cccggacgga gcattgacag g                      41

<210> SEQ ID NO 5
<211> LENGTH: 77
<212> TYPE: DNA
<213> ORGANISM: Artificial sequence
<220> FEATURE:
<223> OTHER INFORMATION: Synthetic sequence: Primer sficx3ba
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)

```
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t

<400> SEQUENCE: 5
tatgcggccc agccggccat ggcannktgt nnknnknnkt gcnnknnknn knnktgtnnk    60
gggcggttct ggcgctg                                                  77

<210> SEQ ID NO 6
<211> LENGTH: 13
<212> TYPE: PRT
<213> ORGANISM: Artificial sequence
<220> FEATURE:
<223> OTHER INFORMATION: Synthetic sequence: Semi-random peptide for a
      3x3 library
<220> FEATURE:
<221> NAME/KEY: VARIANT
<222> LOCATION: (6)..(8)
<223> OTHER INFORMATION: Xaa is a random natural amino acid
<220> FEATURE:
<221> NAME/KEY: VARIANT
<222> LOCATION: (10)..(12)
<223> OTHER INFORMATION: Xaa is a random natural amino acid

<400> SEQUENCE: 6

Pro Ala Met Ala Cys Xaa Xaa Xaa Cys Xaa Xaa Xaa Cys
1               5                   10

<210> SEQ ID NO 7
<211> LENGTH: 67
<212> TYPE: DNA
<213> ORGANISM: Artificial sequence
<220> FEATURE:
<223> OTHER INFORMATION: Synthetic sequence: Primer
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t

<400> SEQUENCE: 7
tatgcggccc agccggccat ggcatgtnnk nnknnktgcn nknnknnktg tggcggttct    60
ggcgctg                                                             67

<210> SEQ ID NO 8
<211> LENGTH: 5
```

```
<212> TYPE: PRT
<213> ORGANISM: Artificial sequence
<220> FEATURE:
<223> OTHER INFORMATION: Synthetic sequence: Sequence from first loop of
      5x5 library
<220> FEATURE:
<221> NAME/KEY: VARIANT
<222> LOCATION: (1)..(1)
<223> OTHER INFORMATION: Xaa is a random natural amino acid

<400> SEQUENCE: 8

Xaa Trp Pro Ala Arg
1               5

<210> SEQ ID NO 9
<211> LENGTH: 5
<212> TYPE: PRT
<213> ORGANISM: Artificial sequence
<220> FEATURE:
<223> OTHER INFORMATION: Synthetic sequence: Sequence from second loop
      of 5x5 library

<400> SEQUENCE: 9

Leu His Gln Asp Leu
1               5

<210> SEQ ID NO 10
<211> LENGTH: 13
<212> TYPE: PRT
<213> ORGANISM: Artificial sequence
<220> FEATURE:
<223> OTHER INFORMATION: Synthetic sequence: Sequence of
      Ac-06-34-18(TMB)-NH2 of PCT/EP2012/069897

<400> SEQUENCE: 10

Cys Ser Trp Pro Ala Arg Cys Leu His Gln Asp Leu Cys
1               5                   10

<210> SEQ ID NO 11
<211> LENGTH: 4
<212> TYPE: PRT
<213> ORGANISM: Artificial sequence
<220> FEATURE:
<223> OTHER INFORMATION: Synthetic peptide

<400> SEQUENCE: 11

Trp Pro Ala Arg
1

<210> SEQ ID NO 12
<211> LENGTH: 5
<212> TYPE: PRT
<213> ORGANISM: Artificial sequence
<220> FEATURE:
<223> OTHER INFORMATION: Synthetic peptide

<400> SEQUENCE: 12

Ser Trp Pro Ala Arg
1               5

<210> SEQ ID NO 13
<211> LENGTH: 4
<212> TYPE: PRT
<213> ORGANISM: Artificial sequence
<220> FEATURE:
<223> OTHER INFORMATION: Synthetic peptide

<400> SEQUENCE: 13
```

```
Trp Pro Ala Lys
1

<210> SEQ ID NO 14
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 A
      library

<400> SEQUENCE: 14

Ala Cys Phe Lys His Cys Arg Val Ala Cys Ala
1               5                   10

<210> SEQ ID NO 15
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 A
      library

<400> SEQUENCE: 15

Ala Cys Phe Pro Lys Cys Arg Val Ala Cys Ala
1               5                   10

<210> SEQ ID NO 16
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 A
      library

<400> SEQUENCE: 16

Ala Cys Phe Asp Pro Cys Arg Val Ile Cys Ala
1               5                   10

<210> SEQ ID NO 17
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 A
      library

<400> SEQUENCE: 17

Ala Cys Phe Lys Asn Cys Arg Val Asn Cys Ala
1               5                   10

<210> SEQ ID NO 18
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 A
      library

<400> SEQUENCE: 18

Ala Cys Phe Asn Lys Cys Arg Val Asn Cys Ala
1               5                   10

<210> SEQ ID NO 19
<211> LENGTH: 11
<212> TYPE: PRT
<213> ORGANISM: Artificial sequence
<220> FEATURE:
```

```
<223> OTHER INFORMATION: Synthetic sequence: Bicyclic peptide from 3x3 A
      library

<400> SEQUENCE: 19

Ala Cys Phe Lys Gln Cys Arg Val Asn Cys Ala
1               5                   10

<210> SEQ ID NO 20
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 A
      library

<400> SEQUENCE: 20

Ala Cys Phe Tyr Lys Cys Arg Val Asn Cys Ala
1               5                   10

<210> SEQ ID NO 21
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 A
      library

<400> SEQUENCE: 21

Ala Cys Phe Lys Ala Cys Arg Val Asn Cys Ala
1               5                   10

<210> SEQ ID NO 22
<211> LENGTH: 15
<212> TYPE: PRT
<213> ORGANISM: Artificial sequence
<220> FEATURE:
<223> OTHER INFORMATION: Synthetic sequence: Bicyclic peptide from 5x5
      library

<400> SEQUENCE: 22

Ala Cys Ala Trp Pro Ala Arg Cys Leu Thr Val Asp Leu Cys Ala
1               5                   10                  15

<210> SEQ ID NO 23
<211> LENGTH: 15
<212> TYPE: PRT
<213> ORGANISM: Artificial sequence
<220> FEATURE:
<223> OTHER INFORMATION: Synthetic sequence: Bicyclic peptide from 5x5
      library

<400> SEQUENCE: 23

Ala Cys Arg Trp Pro Ala Arg Cys Val His Gln Asp Leu Cys Ala
1               5                   10                  15

<210> SEQ ID NO 24
<211> LENGTH: 15
<212> TYPE: PRT
<213> ORGANISM: Artificial sequence
<220> FEATURE:
<223> OTHER INFORMATION: Synthetic sequence: Bicyclic peptide from 5x5
      library

<400> SEQUENCE: 24

Ala Cys Ser Trp Pro Ala Arg Cys Asn His Gln Asp Leu Cys Ala
1               5                   10                  15
```

-continued

```
<210> SEQ ID NO 25
<211> LENGTH: 15
<212> TYPE: PRT
<213> ORGANISM: Artificial sequence
<220> FEATURE:
<223> OTHER INFORMATION: Synthetic sequence: Bicyclic peptide from 5x5
      library

<400> SEQUENCE: 25

Ala Cys Arg Trp Pro Ala Arg Cys Leu Thr Thr Ser Leu Cys Ala
1               5                   10                  15

<210> SEQ ID NO 26
<211> LENGTH: 15
<212> TYPE: PRT
<213> ORGANISM: Artificial sequence
<220> FEATURE:
<223> OTHER INFORMATION: Synthetic sequence: Bicyclic peptide from 5x5
      library

<400> SEQUENCE: 26

Ala Cys Arg Trp Pro Ala Arg Cys Thr His Gln Asn Tyr Cys Ala
1               5                   10                  15

<210> SEQ ID NO 27
<211> LENGTH: 15
<212> TYPE: PRT
<213> ORGANISM: Artificial sequence
<220> FEATURE:
<223> OTHER INFORMATION: Synthetic sequence: Bicyclic peptide from 5x5
      library

<400> SEQUENCE: 27

Ala Cys Thr Trp Pro Ala Arg Cys Thr His Gln Asn Trp Cys Ala
1               5                   10                  15

<210> SEQ ID NO 28
<211> LENGTH: 15
<212> TYPE: PRT
<213> ORGANISM: Artificial sequence
<220> FEATURE:
<223> OTHER INFORMATION: Synthetic sequence: Bicyclic peptide from 5x5
      library

<400> SEQUENCE: 28

Ala Cys Phe Pro Ser His Asp Cys Asp Gly Arg Arg Met Cys Ala
1               5                   10                  15

<210> SEQ ID NO 29
<211> LENGTH: 15
<212> TYPE: PRT
<213> ORGANISM: Artificial sequence
<220> FEATURE:
<223> OTHER INFORMATION: Synthetic sequence: Bicyclic peptide from 5x5
      library

<400> SEQUENCE: 29

Ala Cys Gly Gly Pro Gln Asn Cys Arg Thr Trp Thr Thr Cys Ala
1               5                   10                  15

<210> SEQ ID NO 30
<211> LENGTH: 15
<212> TYPE: PRT
<213> ORGANISM: Artificial sequence
<220> FEATURE:
<223> OTHER INFORMATION: Synthetic sequence: Bicyclic peptide from 5x5
      library

<400> SEQUENCE: 30
```

```
Ala Cys Asn Trp Pro Tyr Arg Cys Leu His Thr Asp Leu Cys Ala
1               5                   10                  15
```

<210> SEQ ID NO 31
<211> LENGTH: 15
<212> TYPE: PRT
<213> ORGANISM: Artificial sequence
<220> FEATURE:
<223> OTHER INFORMATION: Synthetic sequence: Bicyclic peptide from 5x5
      library

<400> SEQUENCE: 31

```
Ala Cys Ser Trp Pro Tyr Arg Cys Leu His Gln Asp Tyr Cys Ala
1               5                   10                  15
```

<210> SEQ ID NO 32
<211> LENGTH: 15
<212> TYPE: PRT
<213> ORGANISM: Artificial sequence
<220> FEATURE:
<223> OTHER INFORMATION: Synthetic sequence: Bicyclic peptide from 5x5
      library

<400> SEQUENCE: 32

```
Ala Cys Gly Val Pro Tyr Arg Cys Thr His Gln Glu Met Cys Ala
1               5                   10                  15
```

<210> SEQ ID NO 33
<211> LENGTH: 15
<212> TYPE: PRT
<213> ORGANISM: Artificial sequence
<220> FEATURE:
<223> OTHER INFORMATION: Synthetic sequence: Bicyclic peptide from 5x5
      library

<400> SEQUENCE: 33

```
Ala Cys Thr Trp Pro Ala Arg Cys Thr Met Gln Asn Trp Cys Ala
1               5                   10                  15
```

<210> SEQ ID NO 34
<211> LENGTH: 15
<212> TYPE: PRT
<213> ORGANISM: Artificial sequence
<220> FEATURE:
<223> OTHER INFORMATION: Synthetic sequence: Bicyclic peptide from 5x5
      library

<400> SEQUENCE: 34

```
Ala Cys Ala Asp Pro Trp Ala Cys Leu Phe Arg Arg Pro Cys Ala
1               5                   10                  15
```

<210> SEQ ID NO 35
<211> LENGTH: 15
<212> TYPE: PRT
<213> ORGANISM: Artificial sequence
<220> FEATURE:
<223> OTHER INFORMATION: Synthetic sequence: Bicyclic peptide from 5x5
      library

<400> SEQUENCE: 35

```
Ala Cys Ala Trp Pro Ala Arg Cys Leu Thr Thr Ser Leu Cys Gly
1               5                   10                  15
```

<210> SEQ ID NO 36
<211> LENGTH: 15
<212> TYPE: PRT
<213> ORGANISM: Artificial sequence

```
<220> FEATURE:
<223> OTHER INFORMATION: Synthetic sequence: Bicyclic peptide from 5x5
      library

<400> SEQUENCE: 36

Ala Cys Thr Tyr Pro Tyr Lys Cys Leu His Gln Asn Leu Cys Ala
1               5                   10                  15

<210> SEQ ID NO 37
<211> LENGTH: 15
<212> TYPE: PRT
<213> ORGANISM: Artificial sequence
<220> FEATURE:
<223> OTHER INFORMATION: Synthetic sequence: Bicyclic peptide from 5x5
      library

<400> SEQUENCE: 37

Ala Cys Ala Trp Pro Ala Lys Cys Leu Thr Arg Glu Leu Cys Ala
1               5                   10                  15

<210> SEQ ID NO 38
<211> LENGTH: 15
<212> TYPE: PRT
<213> ORGANISM: Artificial sequence
<220> FEATURE:
<223> OTHER INFORMATION: Synthetic sequence: Bicyclic peptide from 5x5
      library

<400> SEQUENCE: 38

Ala Cys Gly Gly Tyr Asn Asn Cys Arg Ala Phe Ser Tyr Cys Ala
1               5                   10                  15

<210> SEQ ID NO 39
<211> LENGTH: 13
<212> TYPE: PRT
<213> ORGANISM: Artificial sequence
<220> FEATURE:
<223> OTHER INFORMATION: Synthetic sequence: Ac-06-34-18(TMB)-NH2
      derivative of PCT/EP2012/069897

<400> SEQUENCE: 39

Cys Ser Ala Ala Ala Arg Cys Leu His Gln Asp Leu Cys
1               5                   10

<210> SEQ ID NO 40
<211> LENGTH: 13
<212> TYPE: PRT
<213> ORGANISM: Artificial sequence
<220> FEATURE:
<223> OTHER INFORMATION: Synthetic sequence: Ac-06-34-18(TMB)-NH2
      derivative of PCT/EP2012/069897

<400> SEQUENCE: 40

Cys Ser Ala Gln Ala Arg Cys Leu His Gln Asp Leu Cys
1               5                   10

<210> SEQ ID NO 41
<211> LENGTH: 13
<212> TYPE: PRT
<213> ORGANISM: Artificial sequence
<220> FEATURE:
<223> OTHER INFORMATION: Synthetic sequence: Ac-06-34-18(TMB)-NH2
      derivative of PCT/EP2012/069897

<400> SEQUENCE: 41

Cys Pro Ser Ala Trp Arg Cys Leu His Gln Asp Leu Cys
1               5                   10
```

<210> SEQ ID NO 42
<211> LENGTH: 13
<212> TYPE: PRT
<213> ORGANISM: Artificial sequence
<220> FEATURE:
<223> OTHER INFORMATION: Synthetic sequence: Ac-06-34-18(TMB)-NH2
      derivative of PCT/EP2012/069897

<400> SEQUENCE: 42

Cys Trp Ala Ser Pro Arg Cys Leu His Gln Asp Leu Cys
1               5                   10

<210> SEQ ID NO 43
<211> LENGTH: 13
<212> TYPE: PRT
<213> ORGANISM: Artificial sequence
<220> FEATURE:
<223> OTHER INFORMATION: Synthetic sequence: Ac-06-34-18(TMB)-NH2
      derivative of PCT/EP2012/069897

<400> SEQUENCE: 43

Cys Ala Pro Trp Ser Arg Cys Leu His Gln Asp Leu Cys
1               5                   10

<210> SEQ ID NO 44
<211> LENGTH: 13
<212> TYPE: PRT
<213> ORGANISM: Artificial sequence
<220> FEATURE:
<223> OTHER INFORMATION: Synthetic sequence: Ac-06-34-18(TMB)-NH2
      derivative of PCT/EP2012/069897

<400> SEQUENCE: 44

Cys Trp Ala Arg Ser Pro Cys Leu His Gln Asp Leu Cys
1               5                   10

<210> SEQ ID NO 45
<211> LENGTH: 15
<212> TYPE: PRT
<213> ORGANISM: Artificial sequence
<220> FEATURE:
<223> OTHER INFORMATION: Synthetic sequence: Bicyclic peptide phage
      library 5x5
<220> FEATURE:
<221> NAME/KEY: VARIANT
<222> LOCATION: (3)..(7)
<223> OTHER INFORMATION: Xaa is a random amino acid
<220> FEATURE:
<221> NAME/KEY: VARIANT
<222> LOCATION: (9)..(13)
<223> OTHER INFORMATION: Xaa is a random amino acid

<400> SEQUENCE: 45

Ala Cys Xaa Xaa Xaa Xaa Xaa Cys Xaa Xaa Xaa Xaa Xaa Cys Ala
1               5                   10                  15

<210> SEQ ID NO 46
<211> LENGTH: 11
<212> TYPE: PRT
<213> ORGANISM: Artificial sequence
<220> FEATURE:
<223> OTHER INFORMATION: Synthetic sequence: Bicyclic peptide phage
      library 3x3 A
<220> FEATURE:
<221> NAME/KEY: VARIANT
<222> LOCATION: (3)..(5)
<223> OTHER INFORMATION: Xaa is a random amino acid
<220> FEATURE:
<221> NAME/KEY: VARIANT
<222> LOCATION: (7)..(9)

```
<223> OTHER INFORMATION: Xaa is a random amino acid

<400> SEQUENCE: 46

Ala Cys Xaa Xaa Xaa Cys Xaa Xaa Xaa Cys Ala
1               5                   10

<210> SEQ ID NO 47
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 B
      library

<400> SEQUENCE: 47

Ser Cys Phe Asn Arg Cys Arg Val Pro Cys Phe
1               5                   10

<210> SEQ ID NO 48
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 B
      library

<400> SEQUENCE: 48

Lys Cys Phe Thr Ala Cys Arg Val Asp Cys Phe
1               5                   10

<210> SEQ ID NO 49
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 B
      library

<400> SEQUENCE: 49

Arg Cys Phe Asn Leu Cys Arg Val Gly Cys Leu
1               5                   10

<210> SEQ ID NO 50
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 B
      library

<400> SEQUENCE: 50

Asp Cys Phe Gln Gly Cys Arg Val Phe Cys Ser
1               5                   10

<210> SEQ ID NO 51
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 B
      library

<400> SEQUENCE: 51

Gln Cys Phe Glu Leu Cys Arg Val Val Cys Leu
1               5                   10

<210> SEQ ID NO 52
```

```
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 B
      library

<400> SEQUENCE: 52

Met Cys Phe Asp Ser Cys Arg Val Asn Cys Thr
1               5                   10

<210> SEQ ID NO 53
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 B
      library

<400> SEQUENCE: 53

Ser Cys Phe Ala Leu Cys Arg Val Pro Cys Gln
1               5                   10

<210> SEQ ID NO 54
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 B
      library

<400> SEQUENCE: 54

Val Cys Phe Pro Leu Cys Arg Val Pro Cys Ile
1               5                   10

<210> SEQ ID NO 55
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 B
      library

<400> SEQUENCE: 55

Val Cys Phe Gly Val Cys Arg Val Leu Cys Ala
1               5                   10

<210> SEQ ID NO 56
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 B
      library

<400> SEQUENCE: 56

Lys Cys Phe Gln Ala Cys Arg Val Ser Cys Tyr
1               5                   10

<210> SEQ ID NO 57
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 B
      library

<400> SEQUENCE: 57
```

```
Val Cys Phe Ser Leu Cys Arg Ala Gly Cys Leu
1               5                   10
```

<210> SEQ ID NO 58
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 B
      library

<400> SEQUENCE: 58

```
Arg Cys Phe Glu Lys Cys Arg Ala Phe Cys Tyr
1               5                   10
```

<210> SEQ ID NO 59
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 B
      library

<400> SEQUENCE: 59

```
Arg Cys Trp Gln Thr Cys Arg Val Ser Cys Val
1               5                   10
```

<210> SEQ ID NO 60
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 B
      library

<400> SEQUENCE: 60

```
Leu Cys Trp Thr Gly Cys Arg Val Ser Cys Phe
1               5                   10
```

<210> SEQ ID NO 61
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 B
      library

<400> SEQUENCE: 61

```
Gly Cys Trp Ala Pro Cys Arg Val Gly Cys Tyr
1               5                   10
```

<210> SEQ ID NO 62
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 B
      library

<400> SEQUENCE: 62

```
Arg Cys Trp Thr Ala Cys Arg Gly Leu Cys Phe
1               5                   10
```

<210> SEQ ID NO 63
<211> LENGTH: 11
<212> TYPE: PRT
<213> ORGANISM: Artificial sequence
<220> FEATURE:

```
<223> OTHER INFORMATION: Synthetic sequence: Bicyclic peptide from 3x3 B
      library

<400> SEQUENCE: 63

Asp Cys Tyr Gln Leu Cys Arg Val Ser Cys Glu
1               5                   10

<210> SEQ ID NO 64
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 B
      library

<400> SEQUENCE: 64

Thr Cys Phe Arg Ser Cys Lys Val Ala Cys Tyr
1               5                   10

<210> SEQ ID NO 65
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 B
      library

<400> SEQUENCE: 65

Gln Cys Phe Gln Ala Cys Lys Thr Leu Cys Trp
1               5                   10
```